United States Patent
Nakase

(10) Patent No.: US 9,926,348 B2
(45) Date of Patent: Mar. 27, 2018

(54) METHOD FOR PRODUCING FIBROIN-LIKE PROTEIN

(71) Applicants: AJINOMOTO CO., INC., Tokyo (JP); SPIBER INC., Yamagata (JP)

(72) Inventor: Kentaro Nakase, Kanagawa (JP)

(73) Assignees: Ajinomoto Co., Inc., Tokyo (JP); Spiber Inc., Yamagata (JP)

( * ) Notice: Subject to any disclaimer, the term of this patent is extended or adjusted under 35 U.S.C. 154(b) by 0 days.

(21) Appl. No.: 15/356,818

(22) Filed: Nov. 21, 2016

(65) Prior Publication Data

US 2017/0066804 A1 Mar. 9, 2017

Related U.S. Application Data

(63) Continuation of application No. PCT/JP2015/064653, filed on May 21, 2015.

(30) Foreign Application Priority Data

May 21, 2014 (JP) ................................ 2014-105621

(51) Int. Cl.

| C12P 21/02 | (2006.01) |
|---|---|
| C07K 14/435 | (2006.01) |
| C12N 15/70 | (2006.01) |
| C12N 15/09 | (2006.01) |

(52) U.S. Cl.
CPC ........ *C07K 14/43518* (2013.01); *C12N 15/70* (2013.01); *C12P 21/02* (2013.01); *C12N 15/09* (2013.01)

(58) Field of Classification Search
None
See application file for complete search history.

(56) References Cited

U.S. PATENT DOCUMENTS

2014/0058066 A1 2/2014 Sekiyama et al.

FOREIGN PATENT DOCUMENTS

| JP | 2013-085531 A | 5/2013 |
|---|---|---|
| JP | 2013-188141 A | 9/2013 |
| JP | 2014-124135 A | 7/2014 |
| WO | WO89/04365 A1 | 5/1989 |
| WO | WO2004/003175 A2 | 1/2004 |
| WO | WO2004/003175 A3 | 1/2004 |
| WO | WO2006/008163 A2 | 1/2006 |
| WO | WO2012/165476 A1 | 12/2012 |

OTHER PUBLICATIONS

International Search Report for PCT Patent App. No. PCT/JP2015/064653 (Jul. 28, 2015).
Han, K., et al., "Acetic Acid Formation in *Escherichia coli* Fermentation," Biotechnol. Bioeng. 1992;39:663-671.
Jensen, E. B., et al., "Production of Recombinant Human Growth Hormone in *Escherichia coil*: Expression of Different Precursors and Physiological Effects of Glucose, Acetate, and Salts," Biotechnol. Bioeng. 1990;36:1-11.
San, K.-Y., et al., "Strategies in High-Level Expression of Recombinant Protein in *Escherichia coli*," Annals New York Academy of Sciences, 1994, vol. 721, pp. 257-267.
Shiloach, J., et al., "Effect of Glucose Supply Strategy on Acetate Accumulation, Growth, and Recombinant Protein Production by *Escherichia coli* BL21 (λDE3) and *Escherichia coli* JM109," Biotechnol. Bioeng. 1996;49:421-428.
Shimizu, N., et al., "Fed-Batch Cultures of Recombinant *Escherichia coli* with Inhibitory Substance Concentration Monitoring," J. Ferment. Technol. 1988;66(2):187-191.
International Preliminary Report on Patentability for PCT Patent App. No. PCT/JP2015/064653 (dated Dec. 1, 2016).
Fruchtl, M. S., "Expression, Production, and Purification of Novel Therapeutic Proteins," retrieved from the Internet: URL:http://scholarworks.uark.edu/cgi/viewcontent.cgi?article=1700 &context=etd [retrieved on Nov. 27, 2017], XP002776064, 2013, pp. 8-13.
Extended European Search Report for European Patent App. No. 15796551.8 (dated Dec. 18, 2017).

*Primary Examiner* — James S Ketter
(74) *Attorney, Agent, or Firm* — Cermak Nakajima & McGowan LLP; Shelly Guest Cermak

(57) ABSTRACT

A method for producing a fibroin-like protein is described. A fibroin-like protein is produced by culturing *Escherichia coli* having a gene encoding the fibroin-like protein in a medium, inducing expression of the gene encoding the fibroin-like protein, and collecting the fibroin-like protein, wherein the accumulation of an organic acid at the time of inducing the expression is reduced.

7 Claims, 11 Drawing Sheets

[Fig. 1]
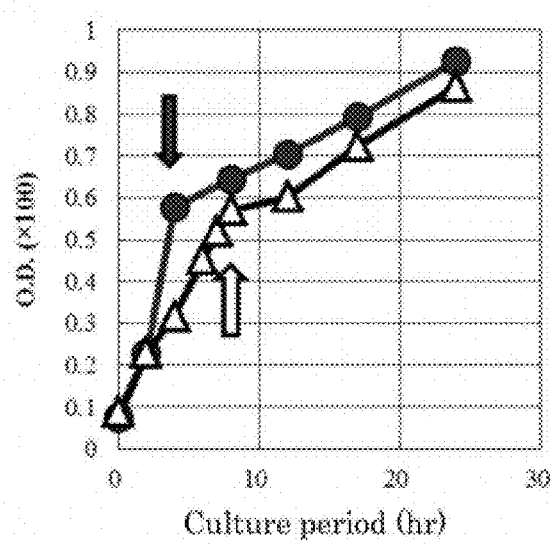
[Fig. 2]
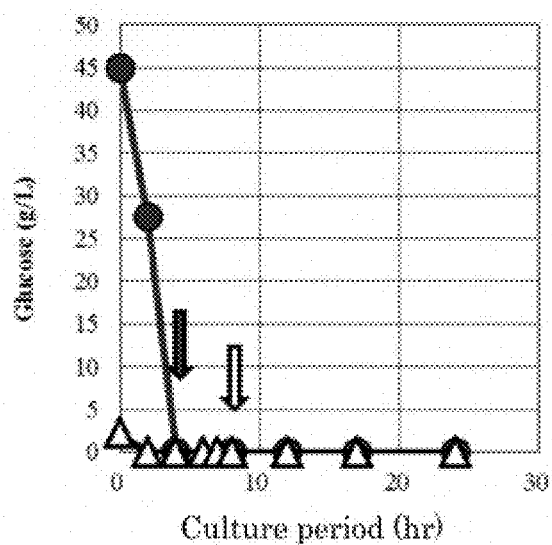

[Fig. 3]
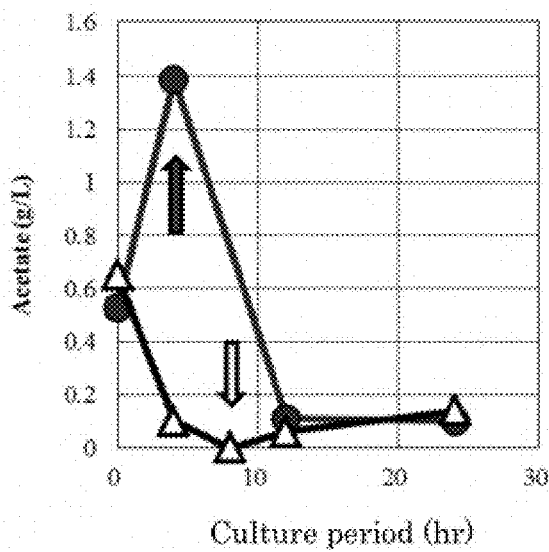
[Fig. 4]
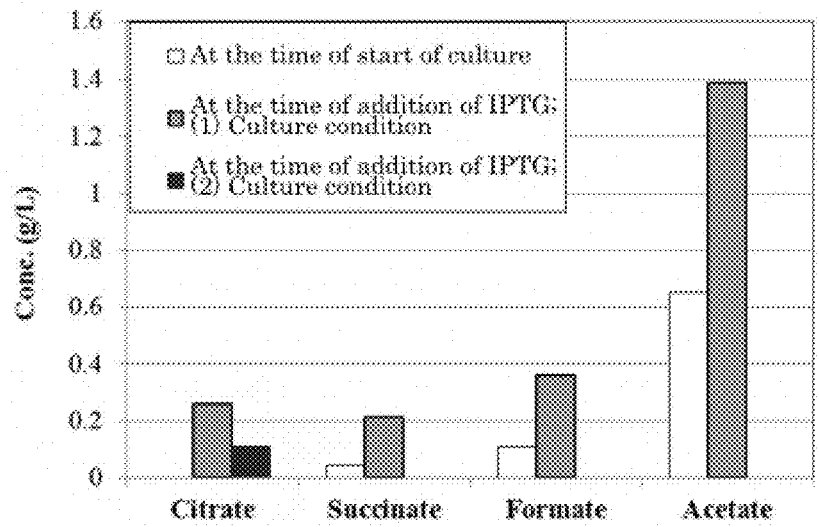

[Fig. 5]
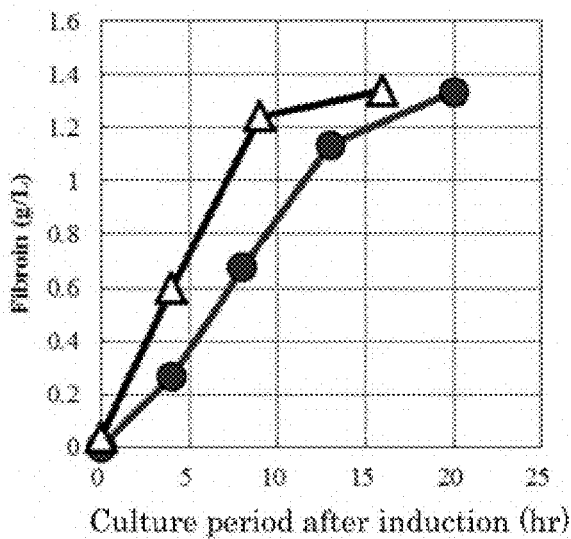
[Fig. 6]
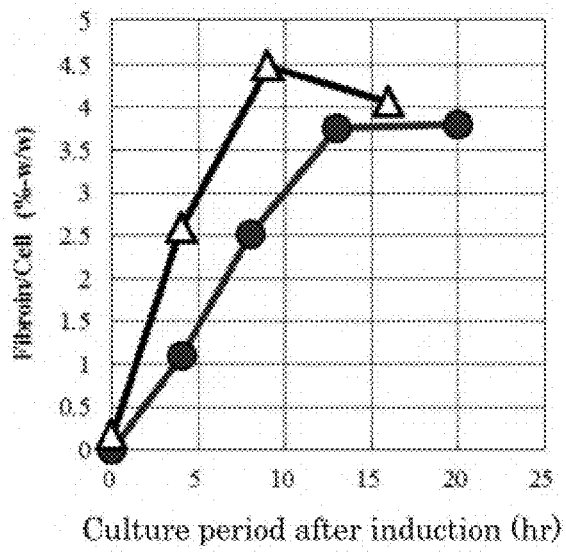

[Fig. 7]
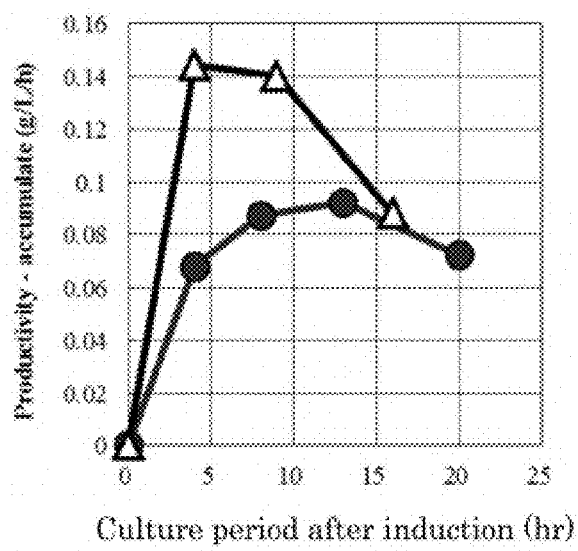
[Fig. 8]
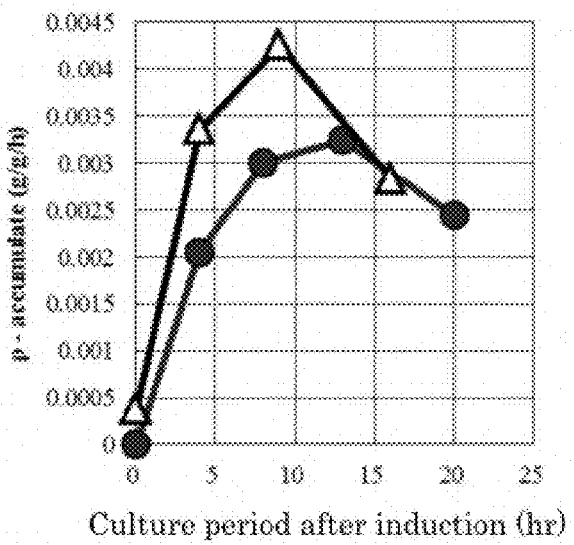

[Fig. 9]
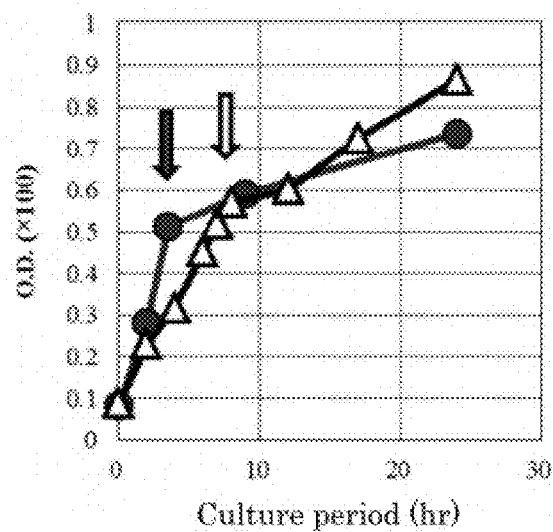
[Fig. 10]
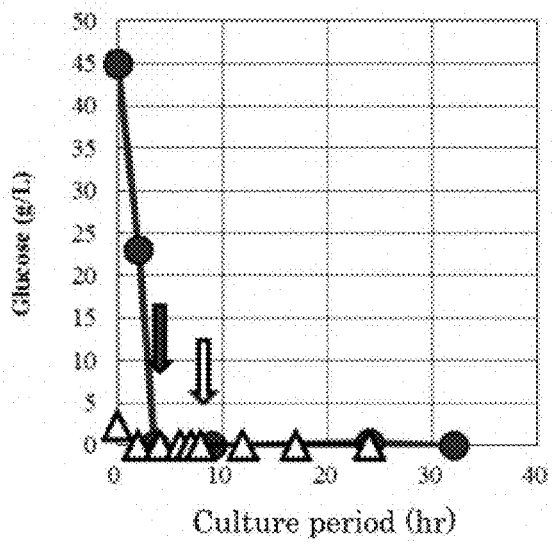

[Fig. 11]
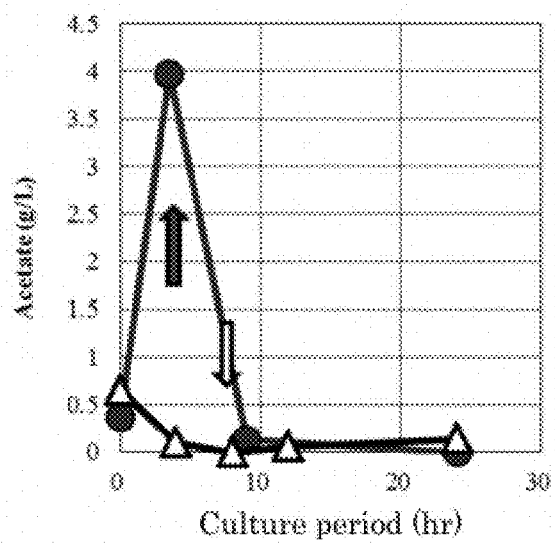
[Fig. 12]
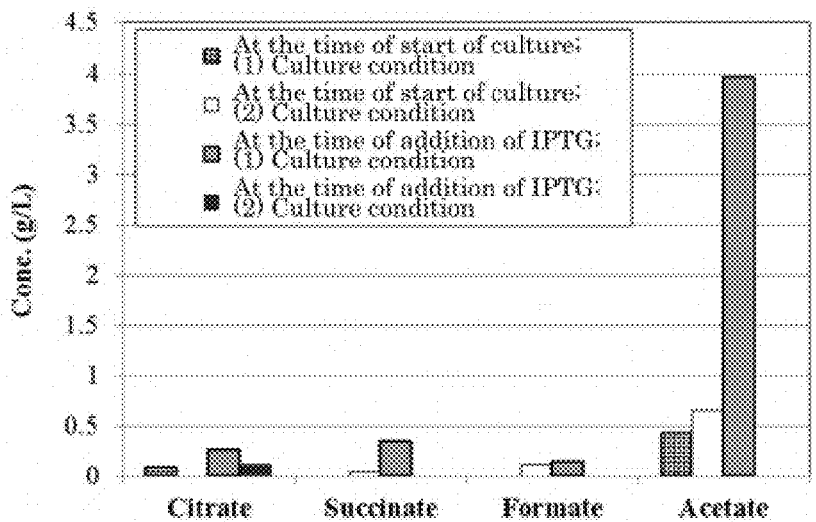

[Fig. 13]
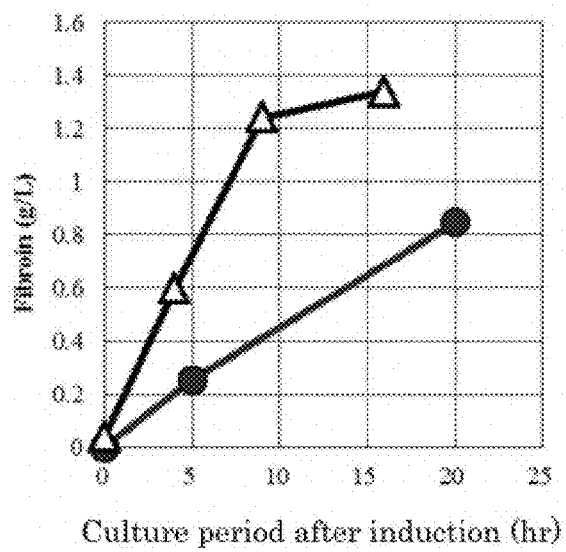
[Fig. 14]
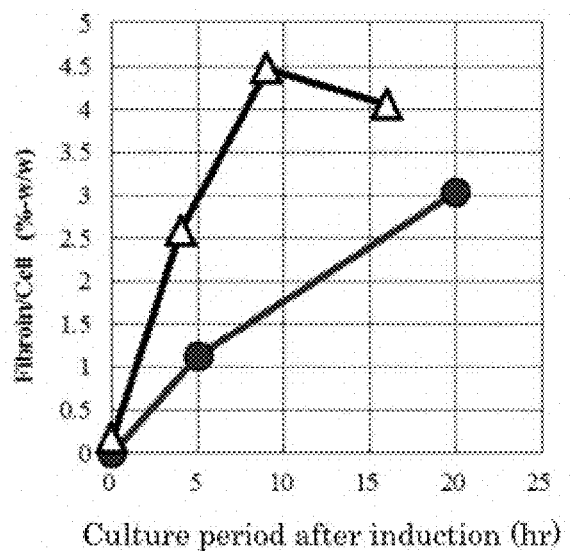

[Fig. 15]
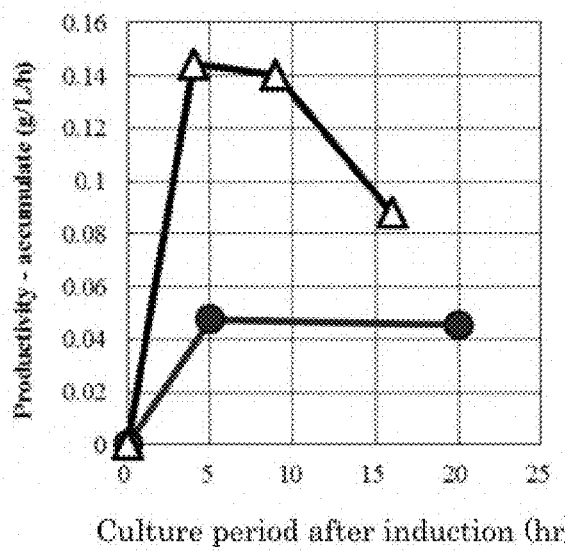
[Fig. 16]
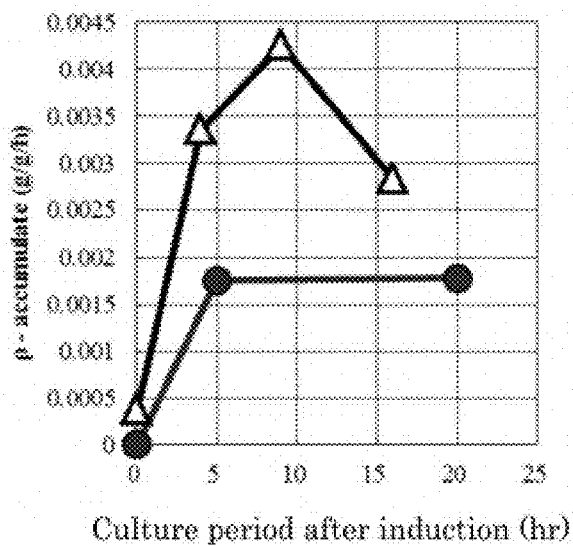

[Fig. 17]
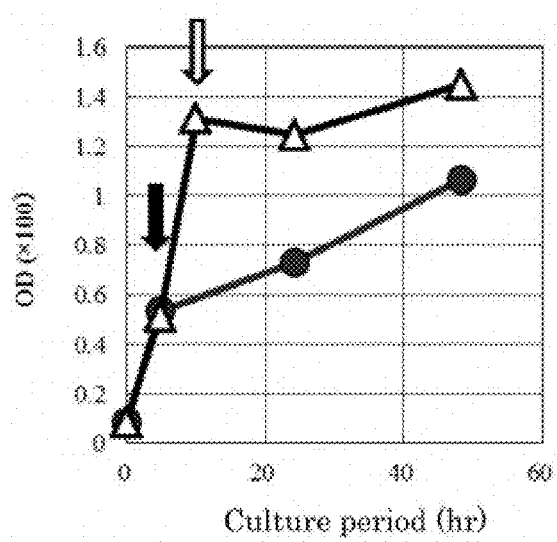
[Fig. 18]
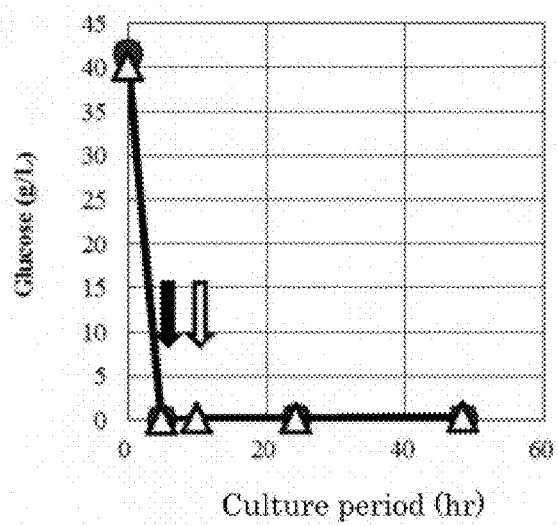

[Fig. 19]
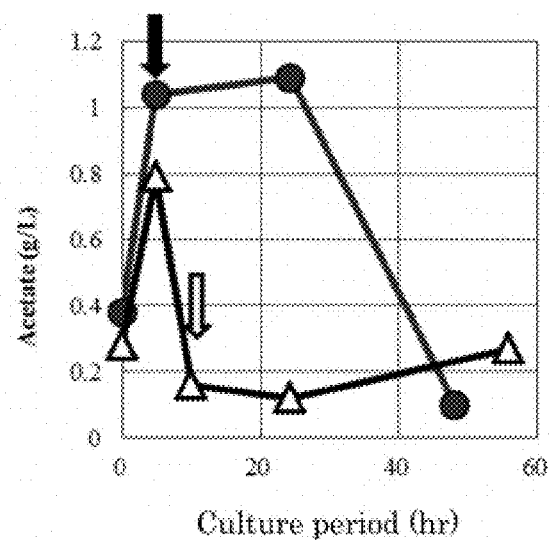
[Fig. 20]
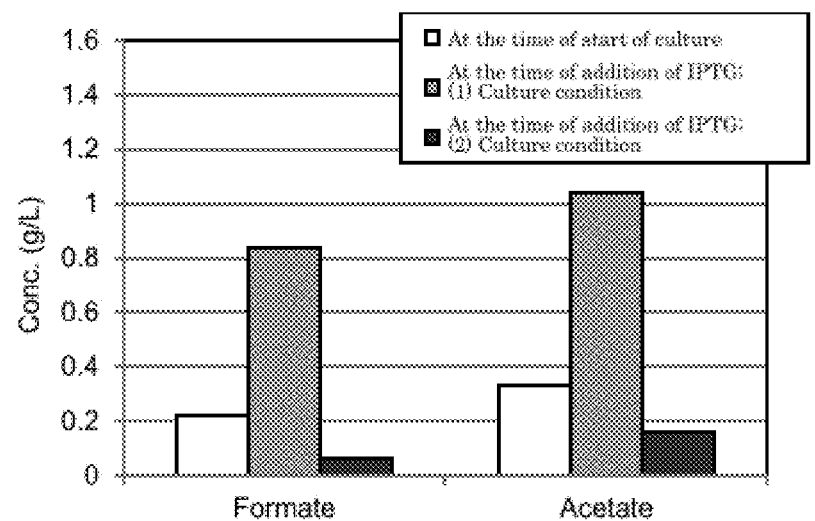

[Fig. 21]
(A)
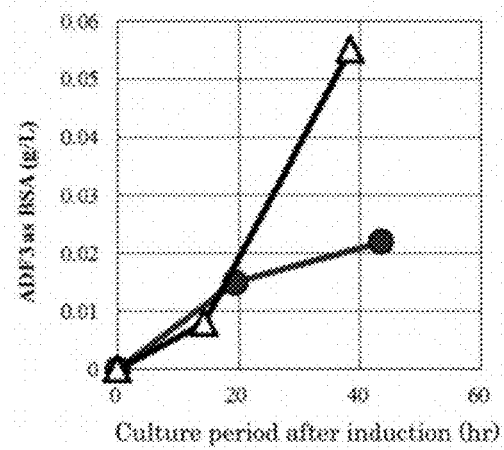
(B)
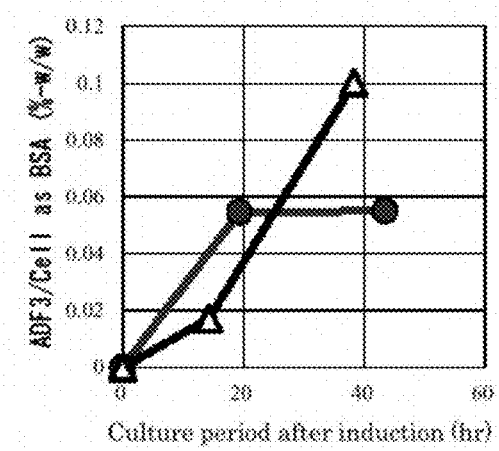
(C)
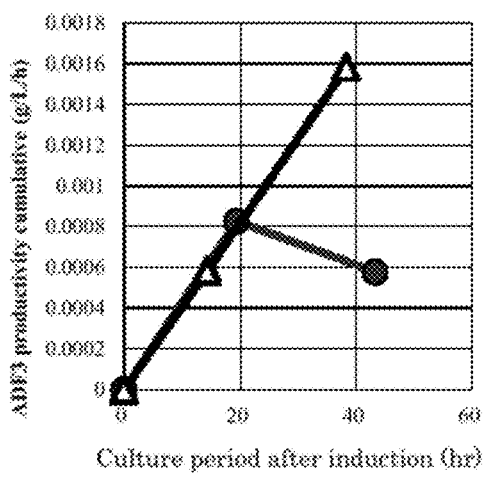

METHOD FOR PRODUCING FIBROIN-LIKE PROTEIN

This application is a Continuation of, and claims priority under 35 U.S.C. § 120 to, International Application No. PCT/JP2015/064653, filed May 21, 2015, and claims priority therethrough under 35 U.S.C. § 119 to Japanese Patent Application No. 2014-105621, filed May 21, 2014, the entireties of which are incorporated by reference herein. Also, the Sequence Listing filed electronically herewith is hereby incorporated by reference (File name: 2016-11-21T_US-556_Seq List; File size: 40 KB; Date recorded: Nov. 21, 2016).

BACKGROUND OF THE INVENTION

Technical Field

The present invention relates to a method for producing a protein such as a fibroin-like protein using heterogeneous expression in *Escherichia coli*.

Background Art

Fibroin is a fibrous protein that is found in spider's thread and silkworm's thread. Spider's thread is a material that is four times stronger than steel, tougher than carbon fiber and aramid fiber, and is highly elastic and resistant to heat. Therefore, the ability to conduct large-scale production of the constituents that make up these threads, such as fibroin or fibrous proteins that are similar in structure to that of fibroin (henceforth generically referred to as "fibroin-like protein").

As for the production of fibroin-like protein, heterogeneous expression thereof using *Escherichia coli* has been reported (see WO2012/165476 and WO2006/008163).

It is also known that, in heterogeneous expression of proteins using *Escherichia coli*, the accumulation of acetic acid in the medium often results in the reduction of cell growth and reduction of the expression amount of protein (see Bech Jensen, E. and Carlsen, S., Biotechnol. Bioeng., 36:1-11, 1990; and Shimizu, N., Fukuzono, S., Fujimori, K., Nishimura, N. and Odawara, Y. J., Ferment. Technol., Vol. 66, No. 2, 187-191, 1988). Namely, when human growth hormone (hGH) is heterogeneously expressed in *Escherichia coli* by continuous culture (chemostat) in which acetic acid concentration is controlled at a certain constant level, the specific production rate of hGH is reduced by about 38% when acetic acid concentration is maintained 2.4 g/L; and if acetic acid concentration exceeded 6.1 g/L, cell growth is also reduced (see Bech Jensen, E. and Carlsen, S., Biotechnol. Bioeng., 36:1-11, 1990). These inhibition effects became more marked under a low pH condition in which the acid is present in a non-dissociated state (see Bech Jensen, E. and Carlsen, S., Biotechnol. Bioeng., 36:1-11, 1990). When β-galactosidase is heterogeneously expressed in *Escherichia coli*, cell growth and accumulation of β-galactosidase are increased by controlling the acetic acid concentration in the medium to be 33 mM or lower in fed-batch culture in which feeding was intermittently stopped when accumulation of acetic is confirmed in the medium (see Shimizu, N., Fukuzono, S., Fujimori, K., Nishimura, N. and Odawara, Y. J., Ferment. Technol., Vol. 66, No. 2, 187-191, 1988). However, none of these references refer or suggest the influence of acetic acid concentration at the time of inducing the expression of a protein.

It is also known that, when *Escherichia coli* is cultured, acetic acid accumulation can be reduced by reducing the glucose uptake rate (Han K., Lim H. C., and Hong J., Biotechnol. Bioeng., March 15; 39(6):663-71, 1992).

SUMMARY OF THE INVENTION

Aspects to be Achieved by the Invention

An aspect of the present invention is to provide an efficient method for producing a protein such as a fibroin-like protein. It has been found that when a fibroin-like protein is heterogeneously expressed in *Escherichia coli*, production of the fibroin-like protein can be improved by reducing the accumulation of organic acid when expression of the fibroin-like protein is induced.

It is an aspect of the present invention to provide a method for producing a protein, the method comprising (A) culturing an *Escherichia coli* bacterium having a gene encoding the protein in a medium; (B) inducing expression of the gene encoding the protein while reducing accumulation of an organic acid; and (C) collecting the protein.

It is another aspect of the present invention to provide a method for producing a fibroin-like protein, the method comprising (A) culturing an *Escherichia coli* bacterium having a gene encoding the fibroin-like protein in a medium; (B) inducing expression of the gene encoding the fibroin-like protein while reducing accumulation of an organic acid; and (C) collecting the fibroin-like protein.

It is another aspect of the present invention to provide the method as described above, wherein the amount of the organic acid present in the medium during step (B) is 4.5 g/L or less.

It is another aspect of the present invention to provide the method as described above, wherein the amount of organic acid, present in the medium during step (B) is 4.0 g/L or less, and wherein the organic acid is acetic acid.

It is another aspect of the present invention to provide the method as described above, wherein said reducing accumulation of the organic acid is initiated by limiting a carbon source in the medium before inducing the expression.

It is another aspect of the present invention to provide the method as described above, wherein concentration of the carbon source in the medium is 0.5 g/L or lower.

It is another aspect of the present invention to provide the method as described above, wherein the carbon source is glucose.

It is another aspect of the present invention to provide the method as described above, wherein said reducing accumulation of the organic acid is achieved by modifying the *Escherichia coli* so that an ability to produce the organic acid is reduced.

It is another aspect of the present invention to provide the method as described above, wherein the organic acid is acetic acid.

BRIEF DESCRIPTION OF THE DRAWINGS

FIG. 1: Graph showing change of OD620 over time. The symbols ● indicate the results obtained with the control condition, and the symbols Δ indicate the results obtained with the glucose-limited condition. The arrows indicate the time points at which an IPTG solution was added.

FIG. 2: Graph showing change of the glucose concentration over time. The symbols ● indicate the results obtained with the control condition, and the symbols Δ indicate the results obtained with the glucose-limited condition. The arrows indicate the time points at which an IPTG solution was added.

FIG. 3: Graph showing change of the acetic acid concentration over time. The symbols ● indicate the results obtained with the control condition, and the symbols Δ indicate the results obtained with the glucose-limited condition. The arrows indicate the time points at which an IPTG solution was added.

FIG. 4: Graph showing the concentrations of organic acids in the medium at the start of the culture and at the time point at which IPTG was added. "(1) Culture condition" means the control condition, and "(2) Culture condition" means the glucose-limited condition.

FIG. 5: Graph showing the accumulation amount of fibroin-like protein relative to volume of the culture medium observed after the addition of an IPTG solution. The symbols ● indicate the results obtained with the control condition, and the symbols Δ indicate the results obtained with the glucose-limited condition.

FIG. 6: Graph showing the accumulation amount of fibroin-like protein relative to cell weight observed after the addition of an IPTG solution. The symbols ● indicate the results obtained with the control condition, and the symbols Δ indicate the results obtained with the glucose-limited condition.

FIG. 7: Graph showing the cumulative productivity of fibroin-like protein observed after the addition of an IPTG solution. The symbols ● indicate the results obtained with the control condition, and the symbols Δ indicate the results obtained with the glucose-limited condition.

FIG. 8: Graph showing the cumulative specific production rate of fibroin-like protein observed after the addition of an IPTG solution. The symbols ● indicate the results obtained with the control condition, and the symbols Δ indicate the results obtained with the glucose-limited condition.

FIG. 9: Graph showing change of OD620 over time. The symbols ● indicate the results obtained with the control condition, and the symbols Δ indicate the results obtained with the glucose-limited condition. The arrows indicate the time points at which an IPTG solution was added.

FIG. 10: Graph showing change of the glucose concentration over time. The symbols ● indicate the results obtained with the control condition, and the symbols Δ indicate the results obtained with the glucose-limited condition. The arrows indicate the time points at which an IPTG solution was added.

FIG. 11: Graph showing change of the acetic acid concentration over time. The symbols ● indicate the results obtained with the control condition, and the symbols Δ indicate the results obtained with the glucose-limited condition. The arrows indicate the time points at which an IPTG solution was added.

FIG. 12: Graph showing the concentrations of organic acids in the medium at the start of the culture and at the time point at which IPTG was added. "(1) Culture condition" means the control condition, and "(2) Culture condition" means the glucose-limited condition.

FIG. 13: Graph showing the accumulation amount of fibroin-like protein relative to volume of the culture medium observed after the addition of an IPTG solution. The symbols ● indicate the results obtained with the control condition, and the symbols Δ indicate the results obtained with the glucose-limited condition.

FIG. 14: Graph showing the accumulation amount of fibroin-like protein relative to cell weight observed after the addition of an IPTG solution. The symbols ● indicate the results obtained with the control condition, and the symbols Δ indicate the results obtained with the glucose-limited condition.

FIG. 15: Graph showing the cumulative productivity of fibroin-like protein observed after the addition of an IPTG solution. The symbols ● indicate the results obtained with the control condition, and the symbols Δ indicate the results obtained with the glucose-limited condition.

FIG. 16: Graph showing the cumulative specific production rate of fibroin-like protein observed after the addition of an IPTG solution. The symbols ● indicate the results obtained with the control condition, and the symbols Δ indicate the results obtained with the glucose-limited condition.

FIG. 17: Graph showing change of OD620 over time. The symbols ● indicate the results obtained with the control condition, and the symbols Δ indicate the results obtained with the glucose-limited condition. The arrows indicate the time points at which an IPTG solution was added.

FIG. 18: Graph showing change of the glucose concentration over time. The symbols ● indicate the results obtained with the control condition, and the symbols Δ indicate the results obtained with the glucose-limited condition. The arrows indicate the time points at which an IPTG solution was added.

FIG. 19: Graph showing change of the acetic acid concentration over time. The symbols ● indicate the results obtained with the control condition, and the symbols Δ indicate the results obtained with the glucose-limited condition. The arrows indicate the time points at which an IPTG solution was added.

FIG. 20: Graph showing the concentrations of organic acids in the medium the start of the culture and at the time point at which IPTG was added. "(1) Culture condition" means the control condition, and "(2) Culture condition" means the glucose-limited condition.

FIG. 21: Graphs showing the results concerning production of wild-type ADF3 after the addition of an IPTG solution: (A) accumulation amount of ADF3 relative to volume of culture medium; (B) accumulation amount of ADF3 relative to cell weight; and (C) cumulative productivity of ADF3. The symbols ● indicate the results obtained with the control condition, and the symbols Δ indicate the results obtained with the glucose-limited condition.

DESCRIPTION OF THE PREFERRED EMBODIMENTS

Hereafter, the present invention will be explained in detail.

<1> Protein to be Produced

The protein to be produced is not particularly limited, so long as it is a protein that can be expressed in an *Escherichia coli* host. The protein may be a protein derived from, or native to, *Escherichia coli*, or may be a heterogeneous protein. Such a heterogeneous protein may be, for example, a protein derived from a microorganism, a protein derived from a plant, a protein derived from an animal, a protein derived from a virus, or an artificially designed protein. The protein may be a monomeric protein, or may be a multimeric protein. The protein may be a secretory protein, or may be a non-secretory protein. The term "protein" includes a peptide, such as oligopeptide and polypeptide.

Examples of the protein to be produced include, for example, fibroin-like proteins, physiologically active proteins, receptor proteins, antigen proteins, and enzymes. A particular example is a fibroin-like protein.

The term "fibroin-like protein" is a generic term referring to fibroin and a fibrous protein having a structure similar to that of fibroin.

The term "fibroin" refers to a fibrous protein that is a component of spider's thread or silkworm's thread. That is, examples of fibroin include spider fibroin, and silkworm fibroin. Species of spider, species of silkworm, and the type of thread are not particularly limited. Examples of spider species include *Araneus diadematus* and *Nephila clavipes*. Examples of spider fibroin include proteins of drag line, frame thread, and radius thread produced by major ampullate gland (major ampullate gland proteins), proteins of scaffolding thread produced by minor ampullate gland (minor ampullate gland proteins), and proteins of spiral line produced by flagelliform gland (flagelliform gland proteins). Specific examples of spider fibroin include, for example, the major ampullate gland proteins ADF3 and ADF4 of *Araneus diadematus* and the major ampullate gland proteins MaSp1 and MaSp2 of *Nephila clavipes*. Examples of silkworm species include *Bombyx mori* and *Samia cynthia*. The amino acid sequences of these fibroins and the nucleotide sequences of the genes encoding these fibroins, also referred to as "fibroin gene", can be obtained from public databases such as NCBI (ncbi.nlm.nih.gov). The amino acid sequence of ADF3 of *Araneus diadematus* (partial; NCBI AAC47010.1 GI: 1263287) is shown as SEQ ID NO: 3. That is, the fibroin-like protein may be, for example, a protein having any of the amino acid sequences of fibroins disclosed in the aforementioned database (for example, SEQ ID NO: 3). A gene encoding a fibroin-like protein, also referred to as "fibroin-like protein gene", may be, for example, a gene having any of the nucleotide sequences of the fibroin genes disclosed in the aforementioned database. The expression "having an amino acid or nucleotide sequence" can include when a larger sequence includes the amino acid or nucleotide sequence, and also when the amino acid or nucleotide sequence is not a part of a larger sequence, but exists alone.

The term "fibrous protein having a structure similar to that of fibroin" can mean a fibrous protein having a sequence similar to a repetitive sequence of fibroin. The "sequence similar to a repetitive sequence of fibroin" may be a sequence actually found in fibroin, or may be a sequence similar to such a sequence. Examples of the fibrous protein having a structure similar to that of fibroin include polypeptides derived from the large spigot drag line proteins described in WO2012/165476 and recombinant spider silk proteins described in WO2006/008163.

Namely, examples of the "sequence similar to a repetitive sequence of fibroin" can include a sequence represented by the following formula I (WO2012/165476, henceforth also referred to as "repetitive sequence I"):

REP1-REP2 (I)

In the formula I, REP1 is an amino acid sequence that is continuous and includes alanine and/or glycine. When REP1 includes both alanine and glycine, the order of alanine and glycine is not particularly limited. For example, in REP1, alanine residues may be continuous and adjacent to each other, glycine residues may be continuous and adjacent to each other, or alanine and glycine residues may alternate. The length of REP1 may be, for example, 2 residues or longer, 3 residues or longer, 4 residues or longer, or 5 residues or longer, or may be 20 residues or shorter, 16 residues or shorter, 13 residues or shorter, 12 residues or shorter, or 8 residues or shorter, or may be within a range defined by any combination of these ranges. The length of REP1 may be, for example, 2 to 20 residues, 3 to 16 residues, 4 to 13 residues, 4 to 12 residues, or 5 to 8 residues. REP1 corresponds to, for example, the crystalline region of the spider fibroin that forms the crystalline β sheet within the fiber.

In the formula I, REP2 is an amino acid sequence that can include one or more of glycine, serine, glutamine, and alanine. In REP2, the total number of glycine, serine, glutamine, and alanine residues may be, for example, 40% or more, 60% or more, or 70% or more of the total number of amino acid residues of REP2. The length of REP2 may be, for example, 2 residues or longer, 10 residues or longer, or 20 residues or longer, or may be 200 residues or shorter, 150 residues or shorter, 100 residues or shorter, or 75 residues or shorter, or may be within a range defined by any combination of these ranges. The length of REP2 may be, for example, 2 to 200 residues, 10 to 150 residues, 20 to 100 residues, or 20 to 75 residues. REP2 corresponds to, for example, an amorphous region of the fibroin of spider showing flexibility, most part of which lacks regular structure.

The number of times the repetitive sequence I repeats is not particularly limited; and can be, for example, 2 or more, 5 or more, or 10 or more, or it can also be 100 or less, 50 or less, or 30 or less, and it may be within a range defined by any combination of these ranges. The configurations of REP1 and REP2 of the respective repetitive sequences may be or may not be the same.

The fibrous protein having a structure similar to that of fibroin can have, for example, an amino acid sequence having a homology of 90% or higher to an amino acid sequence around the C-terminus of the spider fibroin, in addition to the sequence similar to the repetitive sequence of fibroin. Examples of the amino acid sequence around the C-terminus of the fibroin of spider include, for example, the amino acid sequence of the C-terminus 50 residues of the spider fibroin, the amino acid sequence of the C-terminus 50 residues of the same of which the C-terminus 20 residues are removed, and the amino acid sequence of the C-terminus 50 residues of the same of which the C-terminus 29 residues are removed. Specific examples of the amino acid sequence around the C-terminus of the spider fibroin include, for example, the sequence of the positions 587 to 636 (C-terminus 50 residues), the sequence of the positions 587 to 616, and the sequence of the positions 587 to 607 of ADF3 of *Araneus diadematus* (partial; NCBI AAC47010.1 GI: 1263287) shown as SEQ ID NO: 3.

Specific examples of the fibrous protein having a sequence similar to the repetitive sequence of fibroin, and having an amino acid sequence showing a homology of 90% or higher to an amino acid sequence around the C-terminus of the spider fibroin include, for example, a protein encoded by a gene having the nucleotide sequence of SEQ ID NO: 10 described in WO2012/165476A1. The nucleotide sequence of the gene is shown as SEQ ID NO: 1, and the amino acid sequence of the protein encoded by the gene is shown as SEQ ID NO: 2.

The fibroin-like protein may be a variant of any of the fibroin-like proteins exemplified above, that is, fibroin and the fibrous proteins having a structure similar to that of fibroin exemplified above, so long as the original function thereof is maintained. Similarly, the gene encoding the fibroin-like protein may be a variant of any of the fibroin-like protein genes exemplified above, that is, genes encoding fibroin and the fibrous proteins having a structure similar to that of fibroin exemplified above, so long as the original function thereof is maintained. Such variants that maintain the original function are also referred to as "conservative variants". Examples of the conservative variants include, for example, homologues and artificially-modified proteins or genes of the fibroin-like proteins exemplified above and genes encoding them.

The expression that "the original function is maintained" can mean that a variant of a gene or protein has a function, that is, the activity and property, corresponding to the function of the original gene or protein. That is, in the case of the fibroin-like protein, the expression that "the original function is maintained" can mean that a variant of the protein is the fibrous protein. In the case of the fibroin-like protein gene, the expression that "the original function is maintained" means that a variant of the gene encodes a protein that maintains the original function, namely, the fibrous protein. The term "fibrous protein" refers to a protein that has a fibrous form under predetermined conditions. That is, the fibrous protein may be a protein expressed in a fibrous form, or a protein that is not in a fibrous form when it is expressed, but can be processed into a fibrous form. The fibrous protein may be, for example, a protein that is expressed as an inclusion body, and can be then processed into a fibrous form by an appropriate technique.

Examples of homologue of the fibroin-like protein include, for example, a protein obtained from a public database by BLAST search or FASTA search using any of the aforementioned amino acid sequences of fibroin-like proteins as a query sequence. A homologue of the aforementioned fibroin-like protein genes can be obtained by, for example, PCR using a chromosome of various microorganisms as the template, and oligonucleotides prepared on the basis of any of the aforementioned nucleotide sequences of fibroin-like protein genes as the primers.

Conservative variants of the fibroin-like protein and fibroin-like protein gene will be explained below.

The fibroin-like protein may be a protein having any of the aforementioned amino acid sequences of fibroin-like proteins including substitution, deletion, insertion, or addition of one or several amino acid residues at one or several positions, so long as the original function of the protein is maintained. Although the number meant by the term "one or several" can differ depending on the positions of amino acid residues in the three-dimensional structure of the protein, or the types of amino acid residues, it is specifically, for example, 1 to 50, 1 to 40, 1 to 30, 1 to 20, 1 to 10, 1 to 5, and 1 to 3.

The aforementioned substitution, deletion, insertion, or addition of one or several amino acid residues are each a conservative mutation that maintains the original function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Further, such substitution, deletion, insertion, addition, or the like of amino acid residues as mentioned above includes a naturally occurring mutation due to an individual difference, or a difference of species of the organism from which the gene is derived (mutant or variant).

The fibroin-like protein may be a protein having an amino acid sequence showing a homology of 80% or higher, 90% or higher, 95% or higher, 97% or higher, 99% or higher, to any of the aforementioned amino acid sequences of fibroin-like proteins, so long as the original function is maintained. In this description, "homology" can also mean "identity".

The fibroin-like protein may be a protein encoded by a DNA that is able to hybridize under stringent conditions with a probe that can be prepared from any of the aforementioned nucleotide sequences of fibroin-like protein genes, such as a sequence complementary to the whole sequence or a partial sequence of any of the aforementioned nucleotide sequences, so long as the original function is maintained. Such a probe can be prepared by PCR using oligonucleotides prepared on the basis of any of the aforementioned nucleotide sequences as the primers, and a DNA fragment containing any of the aforementioned nucleotide sequences as the template. The "stringent conditions" refer to conditions under which a so-called specific hybrid is formed, and a non-specific hybrid is not formed. Examples of the stringent conditions include those under which highly homologous DNAs hybridize to each other, for example, DNAs not less than 50%, 65%, or 80% homologous, not less than 90% homologous, not less than 95% homologous, not less than 97% homologous, not less than 99% homologous, hybridize to each other, and DNAs less homologous than the above do not hybridize to each other, or conditions of washing of typical Southern hybridization, for example, washing once, or 2 or 3 times, at a salt concentration and temperature of 1×SSC, 0.1% SDS at 60° C., 0.1×SSC, 0.1% SDS at 60° C., or 0.1×SSC, 0.1% SDS at 68° C. Furthermore, for example, when a DNA fragment having a length of about 300 bp is used as the probe, the washing conditions of the hybridization can be, for example, 50° C., 2×SSC, and 0.1% SDS.

The fibroin-like protein may be a fusion protein with another peptide. The "another peptide" is not particularly limited so long as a fibroin-like protein having desired property can be obtained. The "another peptide" can be appropriately selected as required depending on various conditions such as purpose of use thereof. Examples of the "another peptide" include a peptide tag, and recognition sequence for a protease. The "another peptide" may be bound to, for example, the N-terminus or C-terminus, or the both of the fibroin-like protein. As the "another peptide", one kind of peptide may be used, or two or more kinds of peptides may be used in combination.

Specific examples of the peptide tag include an His tag, FLAG tag, GST tag, Myc tag, MBP (maltose binding protein), CBP (cellulose binding protein), TRX (thioredoxin), GFP (green fluorescent protein), HRP (horseradish peroxidase), ALP (alkaline phosphatase), and Fc region of antibody. The peptide tag can be used, for example, for detection and purification of the expressed fibroin-like protein.

Specific examples of the recognition sequence for a protease include the recognition sequence for the HRV3C protease, the recognition sequence for the factor Xa protease, and the recognition sequence for the proTEV protease. The recognition sequence for a protease can be used, for example, for cleavage of the expressed fibroin-like protein. Specifically, for example, when the fibroin-like protein is expressed as a fusion protein with a peptide tag, if a recognition sequence for a protease is introduced into a linking part between the fibroin-like protein and the peptide tag, the peptide tag can be removed from the expressed fibroin-like protein by using the protease to obtain the fibroin-like protein not having the peptide tag.

Specific examples of such a fusion protein include ADF3 of *Araneus diadematus* to which a His tag and the HRV3C protease recognition sequence have been added at the N-terminus (SEQ ID NO: 5). Examples of the nucleotide sequence encoding the fusion protein of SEQ ID NO: 5 include the nucleotide sequence of the positions 12 to 1994 of SEQ ID NO: 4.

The fibroin-like protein gene may have any of the nucleotide sequences of fibroin-like protein genes exemplified above and conservative variants thereof, in which arbitrary codons are replaced with equivalent codons. For example, the fibroin-like protein gene may be modified so that it has codons optimized for codon usage in the chosen host.

When a protein other than the fibroin-like protein is produced, the protein to be produced may be, for example, a protein having a known amino acid sequence, or a conservative variant thereof. The descriptions concerning conservative variants of the fibroin-like protein and the gene encoding it can also be applied mutatis mutandis to other arbitrary proteins and genes encoding them.

<2> Bacterium of the Present Invention

The bacterium is *Escherichia coli* having a gene encoding a protein such as a fibroin-like protein. Although the bacterium will be explained below in reference to producing a fibroin-like protein, the explanations can be also applied mutatis mutandis to production of an arbitrary protein other than fibroin-like protein.

The bacterium has a fibroin-like protein gene, and therefore has an ability to produce a fibroin-like protein (fibroin-like protein-producing ability). The expression that "the bacterium has a fibroin-like protein-producing ability" means that, for example, when the bacterium is cultured in a medium, it produces and accumulates a fibroin-like protein in the medium and/or cells thereof to such an extent that the fibroin-like protein can be collected from the medium and/or cells.

The chosen species/strain of *Escherichia coli* is not particularly limited, and examples thereof include bacteria classified as *Escherichia coli* according to the taxonomy known to those skilled in the field of microbiology. Specific examples of strains of *Escherichia coli* include, for example, *Escherichia coli* K-12 strains such as W3110 (ATCC 27325) and MG1655 (ATCC 47076); *Escherichia coli* K5 (ATCC 23506); *Escherichia coli* B strains such as BL21(DE3) and BLR(DE3), which is an recA$^-$ strain of the former; and derivative strains of these.

These strains are available from, for example, the American Type Culture Collection (Address: P.O. Box 1549, Manassas, Va. 20108, United States of America). That is, registration numbers are given to the respective strains, and the strains can be ordered by using these registration numbers (refer to atcc.org). The registration numbers of the strains are listed in the catalogue of the American Type Culture Collection. The BL21(DE3) strain is available from, for example, Life Technologies (product number C6000-03). The BLR(DE3) strain is available from, for example, Merck Millipore (product number 69053).

The bacterium may be an auxotrophic strain. Such an auxotrophic strain may have one kind of auxotrophy, or may have two or more kinds of auxotrophies. Examples of the auxotrophy include amino acid auxotrophy such as isoleucine auxotrophy, and nucleic acid auxotrophy. For example, the *Escherichia coli* BLR(DE3) strain shows isoleucine auxotrophy (Schmidt M., Romer L., Strehle M., Scheibel T., Biotechnol. Lett., 2007, 29 (11):1741-1744).

An *Escherichia coli* strain having a fibroin-like protein gene can be obtained by introducing the gene into any of the *Escherichia coli* strains as mentioned above. *Escherichia coli* strains that will be transformed with a fibroin-like protein gene and *Escherichia coli* strains that have been transformed with a fibroin-like protein gene are henceforth also generically referred to as "host".

A fibroin-like protein gene can be obtained by cloning from an organism having the fibroin-like protein gene. For the cloning, a nucleic acid such as genomic DNA or cDNA containing the gene can be used. A fibroin-like protein gene can also be obtained by chemical synthesis (Gene, 60(1), 115-127 (1987)).

By appropriately modifying the obtained fibroin-like protein gene, a variant thereof can also be obtained. The gene can be modified by a known technique. For example, an objective mutation can be introduced into a target site of DNA by the site-specific mutation method. That is, for example, a coding region of a gene can be modified by site-specific mutagenesis so that at a specific site in the encoded protein, one or more amino acids is/are substituted, deleted, inserted, or added. Examples of site-specific mutagenesis include PCR (Higuchi, R., 61, in PCR Technology, Erlich, H. A. Eds., Stockton Press (1989); Carter P., Meth., in Enzymol., 154, 382 (1987)), and using a phage (Kramer, W. and Frits, H. J., Meth. in Enzymol., 154, 350 (1987); Kunkel, T. A. et al., Meth. in Enzymol., 154, 367 (1987)).

The method for introducing a fibroin-like protein gene into a host is not particularly limited. In the host, a fibroin-like protein gene may be harbored in such a manner that it can be expressed under control of a promoter that functions in the host. In the host, a fibroin-like protein gene may be present on a vector autonomously replicable out of the chromosome such as plasmid, cosmid, or phagemid, or may be introduced into the chromosome. The host may have only one copy of a fibroin-like protein gene, or may have two or more copies of a fibroin-like protein gene. The host may have only one kind of fibroin-like protein gene, or may have two or more kinds of fibroin-like protein genes.

The promoter for expressing a fibroin-like protein gene is not particularly limited so long as the promoter is a promoter that functions and is inducible in the host. The "promoter that functions and is inducible in a host" refers to a promoter that shows a promoter activity inducible in the host. The promoter may be a promoter derived from, or native to, the host, or a heterogeneous promoter. Examples of promoter that functions and is inducible in *Escherichia coli* include, for example, directly inducible promoters such as lac promoter, trc promoter, tac promoter, trp promoter, araBAD promoter, tetA promoter, rhaP$_{BAD}$ promoter, proU promoter, cspA promoter, λP$_L$ promoter, λP$_R$ promoter, phoA promoter, and pstS promoter, and indirectly inducible promoters such as T3 promoter, T5 promoter, T7 promoter, and SP6 promoter. Gene expression from the lac promoter, trc promoter, or tac promoter can be induced with isopropyl-β-D-thiogalactopyranoside (IPTG) or lactose. Gene expression from the trp promoter can be induced with 3-β-indole acrylate (IAA). Gene expression from the araBAD promoter can be induced with L-arabinose. Gene expression from the tetA promoter can be induced with anhydrotetracycline. Gene expression from the rhaP$_{BAD}$ promoter can be induced with L-rhamnose. Gene expression from the proU promoter can be induced with NaCl. Gene expression from the trp promoter can also be induced by making tryptophan in the medium depleted. Gene expression from the cspA promoter can be induced with low temperature conditions. Gene expression from the λP$_L$ promoter or λP$_R$ promoter can be induced with high temperature conditions. Gene expression from the phoA promoter or pstS promoter can be induced by making phosphate in the medium depleted. Transcription of a gene from the T3 promoter, T5 promoter, T7 promoter, or SP6 promoter is attained with phage T3 RNA polymerase, T5 RNA polymerase, T7 RNA polymerase, or SP6 RNA polymerase, respectively. Therefore, gene expression from the T3 promoter, T5 promoter, T7 promoter, or SP6 promoter can be indirectly induced by inducing expression of a corresponding RNA polymerase under control of such a directly inducible promoter as mentioned above. The aforementioned promoters may be used as they are, or they may be used after being appropriately modified. For example, a highly-active type of such promoters as mentioned above may also be obtained by using various reporter genes, and used. For example, by making the −35 and −10 regions in a promoter region closer to a consensus sequence, the activity of the promoter can be enhanced (WO00/18935). Examples of the highly-active type promoter include various tac-like promoters (Katashkina J I et al., Russian Federation Patent Application No. 2006134574), and the pnlp8 promoter (WO2010/027045). Methods for evaluating the strength of promoters and examples of strong promoters are described in the paper of Goldstein et al. (Prokaryotic Promoters in Biotechnology, Biotechnol. Annu. Rev., 1, 105-128 (1995)), and so forth.

A fibroin-like protein gene can be introduced into a host by, for example, using a vector containing the gene. A vector containing a fibroin-like protein gene is also referred to as a recombinant DNA of a fibroin-like protein gene. The recombinant DNA of a fibroin-like protein gene can be constructed by, for example, ligating a DNA fragment containing the fibroin-like protein gene with a vector that functions in a host. By transforming the host with the recombinant DNA of a fibroin-like protein gene, a transformant harboring the recombinant DNA can be obtained, namely, the gene can be introduced into the host. As the vector, a vector autonomously replicable in the host cell can be used. The vector can be a multi-copy vector. Furthermore, the vector can have a marker such as an antibiotic resistance gene for selection of the transformant. The vector may also contain an inducible promoter for expression of an inserted gene that functions in *Escherichia coli*. The vector may be, for example, a vector derived from a bacterial plasmid, vector derived from a yeast plasmid, vector derived from a bacteriophage, cosmid, phagemid, or the like. Specific examples of vector autonomously replicable in *Escherichia coli* include, for example, pUC19, pUC18, pHSG299, pHSG399, pHSG398, pBR322, pSTV29 (all of these are available from Takara Bio), pACYC184, pMW219 (NIPPON GENE), pTrc99A (Pharmacia), pPROK series vectors (Clontech), pKK233-2 (Clontech), pET series vectors (Novagen), pQE series vectors (QIAGEN), pCold TF DNA (TaKaRa), pACYC, and broad host spectrum vector RSF1010. When such a recombinant DNA is constructed, for example, a coding region of a fibroin-like protein ligated downstream from any one of such promoters as mentioned above may be incorporated into a vector, or a coding region of a fibroin-like protein may be incorporated into a vector downstream from a promoter originally present in the vector.

A fibroin-like protein gene can also be introduced into, for example, a chromosome of a host. A gene can be introduced into a chromosome, for example, by using homologous recombination (Miller, J. H., Experiments in Molecular Genetics, 1972, Cold Spring Harbor Laboratory). Examples of gene transfer method utilizing homologous recombination include, for example, a method of using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, and a transduction method using a phage. Only one copy of the gene may be introduced, or two or more copies of the gene may be introduced. For example, by performing homologous recombination using a sequence which is present in multiple copies on a chromosome as a target, multiple copies of a gene can be introduced into the chromosome. Examples of such a sequence which is present in multiple copies on a chromosome include repetitive DNAs, and inverted repeats located at the both ends of a transposon. Homologous recombination may also be performed by using an appropriate sequence on a chromosome such as a gene unnecessary for carrying out the present invention as a target. Furthermore, a gene can also be randomly introduced into a chromosome by using a transposon or Mini-Mu (Japanese Patent Laid-open (Kokai) No. 2-109985, U.S. Pat. No. 5,882,888, EP 805867 B1). When the gene is introduced into a chromosome, for example, a coding region of a fibroin-like protein ligated downstream from any of such promoters as mentioned above may be incorporated into a chromosome, or a coding region of a fibroin-like protein may be incorporated into a chromosome downstream from a promoter originally present on the chromosome.

Introduction of a gene into a chromosome can be confirmed by, for example, Southern hybridization using a probe having a sequence complementary to the entire gene or a part thereof, or PCR using primers prepared on the basis of the nucleotide sequence of the gene.

The method for the transformation is not particularly limited, and conventionally known methods can be used. Examples of transformation methods include, for example, a method of treating recipient cells with calcium chloride so as to increase permeability thereof for DNA, which has been reported for the *Escherichia coli* K-12 strain (Mandel, M. and Higa, A., J. Mol. Biol., 1970, 53, 159-162), a method of preparing competent cells from cells which are in the growth phase, followed by introducing DNA, which has been reported for *Bacillus subtilis* (Duncan, C. H., Wilson, G. A. and Young, F. E., 1977, Gene, 1:153-167), and so forth. Alternatively, another transformation method includes making DNA-recipient cells into protoplasts or spheroplasts, which can easily take up recombinant DNA, and then introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Furthermore, the electric pulse transformation method has been reported for transforming coryneform bacteria (Japanese Patent Laid-open (Kokai) No. 2-207791).

The bacterium may further be modified so that an ability to produce an organic acid (organic acid-producing ability) is reduced. When two or more kinds of modifications are introduced to the bacterium, the order in which they are introduction is not particularly limited. That is, for example, *Escherichia coli* that has been introduced with a fibroin-like protein gene may be further modified so that the organic acid-producing ability is reduced, or a fibroin-like protein gene may be introduced into *Escherichia coli* that has been modified so that the organic acid-producing ability is reduced.

The expression that "an organic acid-producing ability is reduced" means that, for example, when the bacterium is cultured under typical culture conditions in which an organic acid is a by-product, the amount of the organic acid that accumulates in the medium is smaller than that observed when a control strain is cultured under the same conditions, and may also mean that the organic acid does not accumulate in the medium at all. Examples of the "typical culture conditions under which an organic acid is a by-product" include when the feeding rate of a carbon source into the culture system is higher than the consumption rate of the carbon source by the bacterium in the culture system, that is, in other words, the conditions under which the culture is performed in the presence of a sufficient amount of the carbon source. When the culture is performed in the presence of a sufficient amount of carbon source, the concentration of the carbon source in the culture system is maintained to be high. Therefore, the expression that "culture is performed in the presence of a sufficient amount of carbon source" may mean that the culture is performed so that the concentration of the carbon source in the medium is not lower than a certain concentration. The culture may be performed as batch culture, fed-batch culture, continuous culture, or a combination of these. Examples of the "conditions under which the culture is performed in the presence of a sufficient amount of carbon source" include, for example, conditions wherein concentration in the culture medium is always not lower than a certain concentration from the start of the culture to immediately before inducing the expression. The term "immediately before inducing the expression" may refer to, for example, any time point within a period of from 1 hour before inducing the expression to the induction of of the expression. The term "not lower than a certain concentration" may refer to, for example, a concentration of 0.5 g/L or higher, 1.0 g/L or higher, 2.0 g/L or higher, 3.0 g/L or higher, 5.0 g/L or higher, or 10.0 g/L or higher. Specific examples of the "typical culture condition under which an organic acid is a by-product" include, for example, conditions that the culture is aerobically performed as batch culture by using a liquid medium containing a sufficient amount of glucose such as the control conditions described in the examples. Examples of the control strain include non-modified strains such as wild-type strains and parental strains. Examples of the organic acid include, for example, acetic acid, citric acid, succinic acid, formic acid, and pyruvic acid. In the bacterium, an ability to produce one kind of organic acid may be reduced, or an ability to produce two or more kinds of organic acids may be reduced. Acetic acid is a particular example of the organic acid to be reduced.

Modification for reducing an organic acid-producing ability can be attained by, for example, a mutagenesis treatment. That is, a non-modified strain such as wild-type strain and parental strain can be subjected to a mutagenesis treatment, and a strain showing a reduced organic acid-producing ability can be selected. Examples of the mutagenesis treatment include irradiation of X-ray, irradiation of ultraviolet, and treatment with a mutagenesis agent such as N-methyl-N'-nitro-N-nitrosoguanidine (MNNG), ethyl methanesulfonate (EMS), and methyl methanesulfonate (MMS).

Modification for reducing an organic acid-producing ability can be attained by, for example, reducing the activity of an enzyme of biosynthetic pathway of an organic acid. For example, examples of enzymes of acetic acid biosynthesis pathway include acetate kinase, phosphotransacetylase, pyruvate-formate lyase, pyruvate oxidase, and acetyl Co-A synthetase. The amino acid sequences of these enzymes of various *Escherichia coli* strains and the nucleotide sequences of the genes encoding these enzymes can be obtained from, for example, public databases such as NCBI (ncbi.nlm.nih.gov). In the bacterium, the activity or activities of one kind or two or more kinds of enzymes of biosynthesis pathways of organic acids may be reduced.

Also, for example, by enhancing the phosphoenolpyruvate carboxylase activity, the acetic acid-producing ability can be reduced. The phosphoenolpyruvate carboxylase activity can be enhanced by, for example, increasing the expression of a gene encoding phosphoenolpyruvate carboxylase. Examples of the method for enhancing the expression of a gene include increasing the copy number of the gene, and increasing the transcription or translation of the gene. The copy number of a gene can be increased by introducing the gene into a chromosome of host. The copy number of a gene can also be increased by introducing a vector containing the gene into the host. A gene can be introduced, for example, in the same manner as that of the introduction of a fibroin-like protein gene described above. The transcription or translation of a gene can be increased by modifying an expression control sequence such as promoter, Shine-Dalgarno (SD) sequence (also referred to as ribosome binding site (RBS)), and spacer region between RBS and start codon.

Hereafter, the methods for reducing the activity of a protein such as various enzymes will be explained.

The expression "the activity of a protein is reduced" means that the activity of the protein per cell is reduced as compared with that of a non-modified strain such as a wild-type strain and parent strain. The state that "the activity of a protein is reduced" also includes a state that the activity of the protein has completely disappeared. Specifically, the expression "the activity of a protein is reduced" means that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene, i.e. the amount of mRNA, encoding the protein or the translation amount of the protein, i.e. the amount of the protein. The state that "the number of molecules of the protein per cell is reduced" also includes a state that the protein is not present at all. The state that "the function of each molecule of the protein is reduced" also includes a state that the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0%, as compared with that of a non-modified strain.

The modification for reducing the activity of a protein can be attained by, for example, reducing the expression of a gene encoding the protein. The state that "the expression of a gene is reduced" also includes a state that the gene is not expressed at all. The state that "the expression of a gene is reduced" is also referred to as "the expression of a gene is attenuated". The expression of a gene may be reduced to, for example, 50% or less, 20% or less, 10% or less, 5% or less, or 0%, as compared with that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as promoter, Shine-Dalgarno (SD) sequence (also referred to as ribosome-binding site (RBS)), and spacer region between RBS and the start codon of the gene. When an expression control sequence is modified, one or more nucleotides, two or more nucleotides, or three or more nucleotides, of the expression control sequence are modified. Furthermore, a part or the whole of an expression control sequence may be deleted. The expression of a gene can also be reduced by, for example, manipulating a factor responsible for expression control. Examples of the factor responsible for expression control include low molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described later.

The modification for reducing the activity of a protein can also be attained by, for example, disrupting a gene encoding the protein. Disruption of a gene can be attained by, for example, deleting a part or the whole of the coding region of the gene on a chromosome. Furthermore, the entire gene including sequences upstream and downstream from the gene on a chromosome may be deleted. The region to be deleted may be any region such as an N-terminus region, an internal region, or a C-terminus region, so long as the activity of the protein can be reduced. Deletion of a longer region can usually more surely inactivate the gene. Furthermore, it is preferred that reading frames of the sequences upstream and downstream from the region to be deleted are not the same.

Disruption of a gene can also be attained by, for example, introducing a mutation for an amino acid substitution (missense mutation), a stop codon (nonsense mutation), a frame shift mutation which adds or deletes one or two nucleotide residues, or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another sequence into a coding region of the gene on a chromosome. Site of the insertion may be in any region of the gene, and insertion of a longer region can usually more surely inactivate the gene. It is preferred that reading frames of the sequences upstream and downstream from the insertion site are not the same. The other sequence is not particularly limited so long as a sequence that reduces or eliminates the activity of the encoded protein is chosen, and examples thereof include, for example, a marker gene such as antibiotic resistance genes, and a gene useful for production of an objective substance.

Such modification of a gene on a chromosome as described above can be attained by, for example, preparing a deficient type gene modified so that a part thereof is deleted and thereby it is unable to produce a protein that functions normally, and transforming a host with a recombinant DNA containing the deficient type gene to cause homologous recombination between the deficient type gene and the wild-type gene on a chromosome and thereby substitute the deficient type gene for the wild-type gene on the chromosome. In this procedure, if a marker gene selected according to the characteristics of the host such as auxotrophy is included in the recombinant DNA, the operation becomes easier. The protein encoded by the deficient type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from λ phage (Cho, E. H., Gumport, R. I., Gardner, J. F., J. Bacteriol., 184:5200-5203 (2002)) (refer to WO2005/010175), a method of using a plasmid having a temperature sensitive replication origin, a method of using a plasmid capable of conjugative transfer, a method of utilizing a suicide vector not having a replication origin that functions in a host (U.S. Pat. No. 6,303,383, Japanese Patent Laid-open (Kokai) No. 05-007491), and so forth.

Modification for reducing activity of a protein can also be attained by, for example, a mutagenesis treatment. Examples of the mutagenesis treatment include irradiation of X-ray, irradiation of ultraviolet, and treatment with a mutation agent such as N-methyl-N'-nitro-N-nitrosoguanidine (MNNG), ethyl methanesulfonate (EMS), and methyl methanesulfonate (MMS).

When a protein functions as a complex consisting of multiple subunits, some or all of the subunits may be modified, so long as the activity of the protein is eventually reduced. That is, for example, some or all of a plurality of genes that encode the respective subunits may be disrupted or the like. Furthermore, when there is a plurality of isozymes of a protein, some or all of the activities of the plurality of isozymes may be reduced, so long as the activity of the protein is eventually reduced. That is, for example, some or all of a plurality of genes that encode the respective isozymes may be disrupted or the like.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA include Northern hybridization, RT-PCR, and so forth (Molecular Cloning, Cold Spring Harbor Laboratory Press, Cold Spring Harbor (USA), 2001). The amount of mRNA can be reduced to, for example, 50% or less, 20% or less, 10% or less, 5% or less, or 0%, of that of a non-modified strain.

A reduction in the amount of a protein can be confirmed by Western blotting using antibodies (Molecular Cloning, Cold Spring Harbor Laboratory Press, Cold Spring Harbor (USA) 2001). The amount of the protein can be reduced to, for example, 50% or less, 20% or less, 10% or less, 5% or less, or 0%, of that of a non-modified strain.

Disruption of a gene can be confirmed by determining nucleotide sequence of a part or the whole of the gene, restriction enzyme map, full length, or the like of the gene depending on the means used for the disruption.

<3> Method of the Present Invention

The method of the present invention is a method for producing a protein by culturing *Escherichia coli* having a gene encoding the protein in a medium, inducing expression of the gene encoding the protein, and collecting the protein, wherein production and/or accumulation of an organic acid at the time of inducing the expression is reduced. An embodiment of the method of the present invention is a method for producing a fibroin-like protein by culturing *Escherichia coli* having a gene encoding the fibroin-like protein in a medium, inducing expression of the gene encoding the fibroin-like protein, and collecting the fibroin-like protein, wherein production and/or accumulation of an organic acid at the time of inducing the expression is reduced. Although the method of the present invention will be explained below in reference to producing a fibroin-like protein, the explanations can also be applied mutatis mutandis to production of an arbitrary protein other than fibroin-like protein.

That is, first, culture of the bacterium is started. Expression of the fibroin-like protein gene is induced at an appropriate time after the start of the culture. After the induction of the expression, the culture is further continued to make the bacterium produce and accumulate a fibroin-like protein in the medium and/or cells of the bacterium. The term "time of inducing the expression" refers to the time of performing the induction of the expression, namely, the time of inducing the expression of a gene encoding an objective protein such as a fibroin-like protein gene. The period from the start of the culture to the induction of the expression is also referred to as "period before inducing the expression", and the period from the induction of the expression to the end of the culture is also referred to as "period after inducing the expression".

By the induction of the expression, the expression amount of the gene encoding the objective protein such as a fibroin-like protein gene increases compared with that observed under a normal condition. By the induction of the expression, the expression amount of the gene encoding the objective protein may increase at least 2 times or more, 3 times or more, or 4 times or more, compared with that observed under a normal condition. The term "normal condition" refers to conditions under which the gene encoding the objective protein is expressed under the control of a non-inducible promoter, or conditions under which the induction of the amount of expression appropriate for the chosen expression system does not occur. Examples of the "conditions under which the gene encoding the objective protein is expressed under the control of a non-inducible promoter" include when the gene encoding the objective protein is expressed under the control of a native non-inducible promoter of the gene. Examples of the "conditions under which the induction of the amount of expression appropriate for the chosen expression system does not occur" include, when the expression is induced by the presence of a certain substance, and that substance is not added; when the expression is induced by depletion of a certain substance, and that substance is not depleted; and when the expression is induced at a certain temperature, and the temperature of the culture system is outside the temperature range in which the expression is induced.

Culture conditions are not particularly limited, so long as the bacterium can proliferate during the period before inducing the expression, accumulation of an organic acid at the time of inducing the expression is reduced, and a fibroin-like protein is produced and accumulated during the period after inducing the expression. During the period after inducing the expression, the bacterium may proliferate, or may not proliferate. The culture conditions for the period before inducing the expression and the period after inducing the expression may be the same, or may not be the same. The culture conditions can be appropriately selected by those skilled in the art according to various conditions such as type of the method for reducing accumulation of an organic acid.

The length of "the period before inducing the expression", i.e., the timing for inducing the expression, can be appropriately chosen according to various conditions such as culture conditions. For example, the induction of the expression may be performed at a time point on or after 0 hour, 1 hour, 2 hours, or 3 hours after the start of the culture, or at a time point on or before 240 hours, 200 hours, 160 hours, 120 hours, or 80 hours after the start of the culture, or at a time point within a period defined by any combination of these earliest and latest time points. The induction of the expression may also be performed, for example, when OD620 of the culture medium becomes 40 to 500, 40 to 400, 40 to 300, or 40 to 200. The length of "the period after inducing the expression" can be appropriately chosen according to various conditions such as culture conditions. Culture period after inducing the expression may be, for example, 1 hour or longer, 4 hours or longer, or 8 hours or longer, or may be 240 hours or shorter, 200 hours or shorter, 160 hours or shorter, 120 hours or shorter, or 80 hours or shorter, or may be within a range defined by any combination of these ranges.

The induction of the expression can be performed according to the requirements of the chosen expression system. Namely, the expression of a fibroin-like protein can be induced by adding, to the medium, for example, isopropyl-β-D-thiogalactopyranoside (IPTG) or lactose when the lac promoter, trc promoter, or tac promoter is used; 3-β-indole acrylate (IAA) when the trp promoter is used; L-arabinose when the araBAD promoter is used; anhydrotetracycline when the tetA promoter is used; L-rhamnose when the rhaP$_{BAD}$ promoter is used; or NaCl when the proU promoter is used. The expression of a fibroin-like protein can also be induced by, for example, depleting tryptophan in the medium when the trp promoter is used. The expression of a fibroin-like protein can also be induced by, for example, lowering the temperature of the medium, for example, lowering the temperature to about 15° C., when the cspA promoter is used. The expression of a fibroin-like protein can also be induced by, for example, elevating the temperature of the medium, for example, elevating the temperature to 42° C., when the λP$_L$ promoter or λP$_R$ promoter is used. The expression of a fibroin-like protein can also be induced by, for example, depleting phosphate in the medium when the phoA promoter or pstS promoter is used. When the T3 promoter, T5 promoter, T7 promoter, or SP6 promoter is used, the expression of a fibroin-like protein can also be induced by, for example, appropriately inducing expression of a corresponding RNA polymerase. Furthermore, for example, also when such promoters as mentioned above are modified as required and used, conditions for the induction of the expression can be appropriately chosen. Depending on the configuration of the expression system, two or more kinds of expression induction conditions may be used in combination.

As the medium, for example, media typically used for culture of bacteria such as *Escherichia coli* can be used as is, or after appropriate modification. As the medium, for example, a liquid medium containing a carbon source, nitrogen source, phosphate source, sulfur source, and ingredients such as other various organic and inorganic ingredients as required can be used. Types and concentrations of the medium components may be appropriately chosen by those skilled in the art.

Specific examples of the carbon source include, for example, saccharides such as glucose, fructose, sucrose, lactose, galactose, xylose, arabinose, blackstrap molasses, hydrolysate of starch, and hydrolysate of biomass, organic acids such as acetic acid, fumaric acid, citric acid, succinic acid, and malic acid, alcohols such as glycerol, crude glycerol, and ethanol, and aliphatic acids. As the carbon source, one kind of carbon source may be used, or two or more kinds of carbon sources may be used in combination. Among these, carbon sources other than organic acids can be used, including saccharides and glucose. The ratio of glucose in the total carbon source may be, for example, 50% (w/w) or higher, 70% (w/w) or higher, 90% (w/w) or higher, 95% (w/w) or higher, or 100% (w/w).

Specific examples of the nitrogen source include, for example, ammonium salts such as ammonium sulfate, ammonium chloride, and ammonium phosphate, organic nitrogen sources such as peptone, yeast extract, meat extract, and soybean protein decomposition product, ammonia, and urea. As the nitrogen source, one kind of nitrogen source may be used, or two or more kinds of nitrogen sources may be used in combination.

Specific examples of the phosphate source include, for example, phosphate salts such as potassium dihydrogenphosphate and dipotassium hydrogenphosphate, and phosphoric acid polymers such as pyrophosphoric acid. As the phosphate source, one kind of phosphate source may be used, or two or more kinds of phosphate sources may be used in combination.

Specific examples of the sulfur source include, for example, inorganic sulfur compounds such as sulfates, thiosulfates, and sulfites, and sulfur-containing amino acids such as cysteine, cystine, and glutathione. As the sulfur source, one kind of sulfur source may be used, or two or more kinds of sulfur sources may be used in combination.

Specific examples of the other various organic and inorganic components include, for example, inorganic salts such as sodium chloride, and potassium chloride; trace metals such as iron, manganese, magnesium, and calcium; vitamins such as vitamin B1, vitamin B2, vitamin B6, nicotinic acid, nicotinamide, and vitamin B12; amino acids; nucleic acids; and organic components containing these such as peptone, casamino acid, yeast extract, and soybean protein decomposition product. As the other various organic and inorganic components, one kind of component may be used, or two or more kinds of components may be used in combination.

When an auxotrophic strain that requires a nutrient such as one or more amino acids for growth, the required nutrient can be added to the medium. When a gene is introduced by using a vector carrying an antibiotic resistance gene, the corresponding antibiotic can be added to the medium.

The culture can be aerobically performed by, for example, aeration or shaking. The oxygen concentration may be adjusted to, for example, 5 to 50%, or about 20 to 40%, of the saturated dissolved oxygen concentration. The culture temperature may be, for example, 20 to 45° C., 25 to 40° C., or 30 to 37° C. The pH of the medium may be 5 to 9 during the culture. To adjust the pH, inorganic or organic acidic or alkaline substances such as calcium carbonate, ammonia gas, and aqueous ammonia can be used. The culture can be performed as batch culture, fed-batch culture, continuous culture, or a combination of these. The medium used at the time of the start of the culture is also referred to as "starting medium". The medium supplied to a culture system or a fermentation tank used in fed-batch culture or continuous culture is also referred to as "feed medium". To supply a feed medium to a culture system used in fed-batch culture or continuous culture is also referred to as to "feed". The culture may also be performed as separate pre-culture and main culture. The pre-culture may be performed by using, for example, a plate medium or liquid medium.

Each of the medium components may be contained in the starting medium, feed medium, or both. The components in the starting medium may be or may not be the same as those in the feed medium. The concentrations of the components in the starting medium may be or may not be the same as the concentrations of those in the feed medium. Furthermore, two or more kinds of feed media containing components of different types and/or different concentrations may be used. For example, when feeding is intermittently performed two or more times, types and/or concentrations of components contained in the respective feed media may be or may not be the same.

The method of the present invention is characterized in that accumulation of an organic acid at the time of inducing the expression of a fibroin-like protein is reduced. The expression that "accumulation of an organic acid is reduced" means that the accumulation amount of the organic acid in the medium is smaller than the accumulation amount of the organic acid in the medium observed under control conditions, and may also mean that the organic acid is not accumulated at all in the medium. Examples of the organic acid include, for example, acetic acid, citric acid, succinic acid, formic acid, and pyruvic acid. The accumulation amount of one kind of organic acid may be reduced, or the accumulation amounts of two or more kinds of organic acids may be reduced. Among those acids, the accumulation amount of at least acetic acid can be reduced. The degree of the reduction is not particularly limited so long as production of the fibroin-like protein is improved compared with that observed under control conditions. The expression that "accumulation of an organic acid is reduced" may also mean that the accumulation amount of the organic acid in the medium is, for example, 70% or less, 50% or less, 30% or less, or 10% or less of the accumulation amount of the organic acid in the medium observed under control conditions. The expression that "accumulation of an organic acid is reduced" may also mean that the accumulation amount of the organic acid in the medium (when there are two or more kinds of organic acids, the total amount of them) is, for example, 4.5 g/L or less, 3.0 g/L or less, 2.0 g/L or less, 1.0 g/L or less, 0.5 g/L or less, 0.2 g/L or less, 0.1 g/L or less, or 0 (zero). The expression that "accumulation of an organic acid is reduced" may also mean that the accumulation amount of acetic acid in the medium is, for example, 4.0 g/L or less, 3.5 g/L or less, 2.5 g/L or less, 1.5 g/L or less, 1.0 g/L or less, 0.5 g/L or less, 0.2 g/L or less, 0.1 g/L or less, or 0 (zero). The accumulation amount of an organic acid may be reduced as a result of, for example, reduction in the production amount of the organic acid, consumption of the organic acid once produced, or combination of these.

In the present invention, the term "control conditions" refers to conditions under which accumulation of an organic acid is not reduced. Examples of the "control conditions" include conditions under which a typical strain of *Escherichia coli* is cultured and an organic acid results as a by-product. Examples of such conditions include when the feeding rate of a carbon source into the culture system is higher than the consumption rate of the carbon source by the bacterium in the culture system, that is, in other words, when the culture is performed in the presence of a sufficient amount of the carbon source. When the culture is performed in the presence of a sufficient amount of carbon source, the concentration of the carbon source in the culture system is maintained to be high. Therefore, the expression that "culture is performed in the presence of a sufficient amount of carbon source" may mean that the culture is performed so that the concentration of the carbon source in the medium is not lower than a certain concentration. The culture may be performed as batch culture, fed-batch culture, continuous culture, or a combination of these. Examples of the "conditions that the culture is performed in the presence of a sufficient amount of carbon source" include, for example, conditions that the culture is performed so that glucose concentration in the medium is always not lower than a certain concentration from the start of the culture to immediately before inducing the expression. The term "immediately before inducing the expression" may refer to, for example, any time point within a period of from 1 hour before inducing the expression to the induction of the expression. The term "not lower than a certain concentration" may refer to, for example, a concentration of 0.5 g/L or higher, 1.0 g/L or higher, 2.0 g/L or higher, 3.0 g/L or higher, 5.0 g/L or higher, or 10.0 g/L or higher. Specific examples of the "typical culture condition under which an organic acid is a by-product" include, for example, conditions that the culture is aerobically performed as batch culture by using a liquid medium containing a sufficient amount of glucose such as the control conditions described in the examples of this description. The "typical strain of *Escherichia coli*" is not particularly limited so long as it is an *Escherichia coli* strain not modified so that an organic acid-producing ability is reduced. Examples of the "typical strain of *Escherichia coli*" include, for a case that the bacterium of the present invention is not modified so that an organic acid-producing ability is reduced, the bacterium of the present invention; and for a case that the bacterium of the present invention is modified so that an organic acid-producing ability is reduced, a strain before the modification (i.e. a strain before being modified so that the organic acid-producing ability is reduced).

The expression that "production of the fibroin-like protein is improved compared with that observed under control conditions" means that the value of a parameter that indicates the amount of the fibroin-like protein produced is larger than that observed under the control conditions. The term "parameter that indicates the amount of the fibroin-like protein produced" refers to the accumulation amount of the fibroin-like protein relative to medium volume, the accumulation amount of the fibroin-like protein relative to cell weight, the cumulative productivity of the fibroin-like protein, the cumulative specific production rate (ρ-cumulative) of the fibroin-like protein, or a combination of these. The expression that "production of the fibroin-like protein is improved compared with that observed under control conditions" may mean that, for example, the value of a parameter that indicates the productivity of the fibroin-like protein is 1.1 times or more, 1.2 times or more, 1.3 times or more, 1.4 times or more, or 1.5 times or more of that observed under the control conditions. The value of a parameter that indicates the amount of fibroin-like protein produced may be larger than that observed under the control conditions in terms of, for example, the value observed at a predetermined time point during the period after inducing the expression, or the maximum value observed during the period after inducing the expression. The "predetermined time point" can be appropriately chosen depending on various conditions such as culture conditions. The term "predetermined time point" may refer to, for example, the time point at which accumulation of the fibroin-like protein stops. The term "time point at which accumulation of the fibroin-like protein stops" may refer to, for example, a time point at which increase ratio of the accumulation amount of the fibroin-like protein relative to cell weight becomes 10% or less (lower) per 4 to 12 hours. The term "time point at which accumulation of the fibroin-like protein stops" may also refer to, for example, 4 hours, 9 hours, 14 hours, 21.5 hours, 30 hours, 50 hours, 70 hours, or 100 hours after the induction of the expression, although it changes depending on the culture conditions.

The cumulative productivity of fibroin-like protein from the time of inducing the expression to a predetermined time point is calculated in accordance with the following equation.

$$\text{Cumulative productivity} = F/V/(T_1 - T_0)$$

F: Accumulation amount of fibroin-like protein (g)
V: Volume of medium (L)
$T_1$: Sampling time (predetermined time point)
$T_0$: Time of inducing expression The cumulative specific production rate of fibroin-like protein from the time of inducing the expression to a predetermined time point is calculated in accordance with the following equation.

$$\text{Cumulative specific production rate} (g/(g \cdot h)) = Pt/\int Xtdt$$

t: Time after start of induction (h)
Pt: Accumulation of fibroin at t hours after start of induction
$\int Xtdt$: Integrated cell amount from start of induction to t hours after start of induction (g·h)

The method for reducing accumulation of the organic acid at the time of inducing the expression is not particularly limited.

Accumulation of the organic acid at the time of inducing the expression can be reduced by, for example, performing the culture under limitation of a carbon source (carbon source limitation) during the period before inducing the expression. The term "carbon source limitation" means that supply of a carbon source to a culture system is limited. By the carbon source limitation, the concentration of the carbon source in the culture system may be maintained to be low. That is, the term "carbon source limitation" may mean that, for example, the concentration of the carbon source in a medium is limited to be a certain concentration or lower. The value of the "certain concentration" is not particularly limited so long as production of the fibroin-like protein is improved compared with that observed under the control conditions. The term "certain concentration or lower" may refer to, for example, a concentration of 1.0 g/L or lower, 0.5 g/L or lower, 0.2 g/L or lower, 0.1 g/L or lower, or 0 (zero). The concentration of the carbon source may be limited to be a certain concentration or lower over the entire period of the period before inducing the expression, or during only a partial period of the period before inducing the expression. The length of the "partial period" is not particularly limited so long as production of the fibroin-like protein is improved compared with that observed under the control conditions. The term "partial period" may refer to, for example, a period of 50% or more, 70% or more, 90% or more, or 95% or more of the entire period of the period before inducing the expression. The concentration of the carbon source may be or may not be constant over the entire period of the period before inducing the expression. The carbon source limitation may also be performed during the period after inducing the expression, in addition to the period before inducing the expression.

The carbon source limitation can be performed by feeding a feed medium containing a carbon source so that the concentration of the carbon source in the medium is maintained to be a certain concentration or lower. The concentration of the carbon source in the medium can be maintained to be a certain concentration or lower by, for example, feeding the feed medium so that supply rate (feeding rate) of the carbon source into the culture system is lower than the consumption rate of the carbon source by the bacterium in the culture system. The concentration of the carbon source in the feed medium and the feeding rate of the feed medium are not particularly limited so long as the concentration of the carbon source in the medium can be limited to be a certain concentration or lower. The concentration of the carbon source in the feed medium and the feeding rate of the feed medium can be appropriately chosen depending on various conditions such as culture conditions. The concentration of the carbon source in the feed medium or the feeding rate of the feed medium may be chosen so that, for example, the feeding rate of the carbon source, determined from the concentration of the carbon source in the feed medium and the feeding rate of the feed medium, is 1 to 100 g/hr, 1 to 70 g/hr, 1 to 40 g/hr, 1 to 30 g/hr, or 1 to 20 g/hr per 1 L of the culture medium at the time of the start of the culture. Both the concentration of the carbon source in the feed medium and the feeding rate of the feed medium may be or may not be constant over the period before inducing the expression.

Feeding of the feed medium may be performed continuously or intermittently. Feeding of the feed medium may be started at the time of the start of the culture, or may be started during the culture. Feeding of the feed medium may be started, for example, after the concentration of the carbon source in the medium becomes a certain concentration or lower, specifically, after the carbon source is depleted. When feeding is intermittently performed two or more times, the concentration of the carbon source in the fermentation medium can also be automatically maintained at a low level by controlling the feeding so that the second and following feedings are started when the carbon source in the fermentation medium is depleted in the non-feeding periods immediately before the respective feeding periods (U.S. Pat. No. 5,912,113). Depletion of the carbon source can be detected on the basis of, for example, elevation of pH, or elevation of dissolved oxygen concentration (U.S. Pat. No. 5,912,113).

The feeding of the feed medium is usually performed so that the carbon source is not depleted, or that depletion of carbon source is brief and not continuous. However, the carbon source may be temporarily depleted so long as production of the fibroin-like protein is improved compared with that observed under the control conditions. The term "temporarily" refers to, for example, a period of 30% or less, 20% or less, 10% or less, or 5% or less of the entire period of the period before inducing the expression. The concentration of the carbon source in the medium of 0 (zero) does not necessarily mean that the carbon source is depleted. That is, even if the concentration of the carbon source in the medium is maintained to be 0 (zero), if elevation of pH or elevation of dissolved oxygen concentration is not observed, the carbon source is not depleted. As such a case, there is assumed, for example, a case where although the feeding of the carbon source to the culture system is continued, the concentration of the carbon source in the medium is maintained to be 0 (zero) because of prompt consumption of the fed carbon source.

The concentration of the carbon source in the starting medium is not particularly limited so long as the carbon source limitation can be attained. The concentration of the carbon source in the starting medium may be or may not be a certain concentration or lower. That is, even if the concentration of the carbon source in the starting medium is higher than the certain concentration, it is sufficient that the carbon source in the starting medium is consumed during the culture and thereby the concentration of the carbon source becomes the certain concentration or lower. The concentration of the carbon source in the starting medium may be, for example, 100 g/L or lower, 70 g/L or lower, 50 g/L or lower, 30 g/L or lower, 20 g/L or lower, 10 g/L or lower, 5 g/L or lower, or 2 g/L or lower. The term "starting medium" may be read as "medium at the time of the start of the culture". Specifically, the term "medium at the time of the start of the culture" may refer to the culture medium immediately after inoculation.

Accumulation of the organic acid at the time of inducing the expression can also be reduced by, for example, using a strain modified so that the organic acid-producing ability is reduced.

Any one of such methods for reducing accumulation of the organic acid at the time of inducing the expression may be independently used, or two or more of them may be used in an appropriate combination.

By culturing the bacterium as described above, a fibroin-like protein is accumulated in the medium and/or cells of the bacterium. The fibroin-like protein can be accumulated as, for example, inclusion bodies in the cells.

The fibroin-like protein can be collected and quantified by, for example, known methods for collecting and quantifying a heterogeneously expressed protein (see, for example, "Lecture of New Chemical Experiments, Protein VI, Synthesis and Expression", Ed. By Japanese Biochemical Society, Tokyo Kagaku Dojin, 1992, pp. 183-184).

Hereafter, procedures for collecting and quantifying a fibroin-like protein will be exemplified for a case where the fibroin-like protein is accumulated as inclusion bodies in the cells. First, the cells are collected from the culture medium by centrifugation, and then suspended in a buffer. The cell suspension is subjected to such a treatment as ultrasonication or French press to disrupt the cells. Before disrupting the cells, lysozyme may be added to the cell suspension at a final concentration of 0 to 200 mg/l, and the suspension may be incubated on ice for 30 minutes to 20 hours. Then, an insoluble fraction is obtained from the disrupted cell suspension as precipitates by low speed centrifugation (6000 to 15000 rpm, 5 to 10 minutes, 4° C.). The insoluble fraction is appropriately washed with a buffer as required. The number of times of washing is not be particularly limited, and may be, for example, once, twice, or 3 times or more. By suspending the insoluble fraction in a buffer, a suspension of the fibroin-like protein is obtained. As the buffer for suspending the cells or fibroin-like protein, a buffer in which the fibroin-like protein shows a low solubility can be used. Examples of such a buffer include, for example, a buffer containing 20 mM Tris-HCl, 30 mM NaCl, and 10 mM EDTA, and a buffer containing 20 mM Tris-HCl and 30 mM NaCl. pH of the buffer may be, for example, usually 4 to 12, or 6 to 9. A solution of the fibroin-like protein can also be obtained by dissolving the insoluble fraction in an SDS solution or urea solution. The collected fibroin-like protein may contain such components as bacterial cells, medium components, and bacterial metabolic by-products, in addition to the fibroin-like protein. The fibroin-like protein may be purified to a desired degree. The amount of the fibroin-like protein can be determined, for example, as follows: a sample containing the fibroin-like protein such as suspension or solution is subjected to SDS-PAGE, and stained, and then, the amount of the fibroin-like protein can be determined on the basis of intensity of a band at the position corresponding to the molecular weight of the objective fibroin-like protein. The staining can be performed by CBB staining, fluorescence staining, silver staining, or the like. For the quantification, proteins of known concentrations can be used as the standards. Examples of such proteins include, for example, albumin and a fibroin-like protein, the concentrations of which can be separately determined.

The fibroin-like protein obtained as described above can be subjected to fibrillation or the like as required, and then used. Fibrillation of a fibroin-like protein can be performed by, for example, a known method. Specifically, fibrillation of a fibroin-like protein can be performed with reference to, for example, the descriptions concerning fibrillation of polypeptides originating in large spigot drag line proteins described in WO2012/165476.

EXAMPLES

Hereafter, the present invention will be more specifically explained with reference to the following non-limiting examples.

Reference Example 1

Construction of Fibroin-Like Protein-Producing Strain

The strain and gene used for the production of fibroin-like protein in the examples (Examples 1 and 2) are as follows.
Host: *Escherichia coli* BLR(DE3)
Vector: pET22b(+)
Fibroin-like protein gene: Gene having the nucleotide sequence described in WO2012/165476A1 as SEQ ID NO: 10
A fibroin-like protein-producing bacterium can be obtained by transforming *Escherichia coli* BLR(DE3) with the pET22b(+) vector (WO2012/165476A1) carrying the aforementioned gene. The nucleotide sequence of the aforementioned gene and the amino acid sequence of the fibroin-like protein encoded by the gene are shown as SEQ ID NOS: 1 and 2, respectively.

Reference Example 2

Preparation of Seed Culture Broth

To 300 ml of the seed culture medium (Table 1) contained in a jar fermenter, the host bacterium was inoculated at an OD620 of 0.005. OD620 was measured with a spectrophotometer UV-mini1240 (Shimadzu). Culture was performed while maintaining the temperature of the culture medium at 37° C., aerating with 300 mL per 1 minute of air disinfected with a filter, stirring at 1500 rpm, and maintaining the pH of the culture medium at a constant pH of 6.7 by appropriately blowing ammonia gas into the medium. During the culture, the culture medium was periodically sampled, and the glucose concentration in the culture medium was measured by using BF-5 (Oji Scientific Instruments). After 12 hours, that is at the time point when glucose in the medium for seed culture was completely consumed, the culture was terminated to obtain a seed culture broth.

TABLE 1

| Medium for seed culture (per 1 L at the time of start of culture) | |
| --- | --- |
| Glucose | 40 g |
| $KH_2PO_4$ | 2 g |
| $MgSO_4 \cdot 7H_2O$ | 1 g |
| CSL | 1 g (as nitrogen amount) |
| $FeSO_4 \cdot 7H_2O$ | 10 mg |
| $MnSO_4 \cdot 5H_2O$ | 10 mg |
| Isoleucine | 1 g |
| GD-113 (anti-foaming agent) | 0.1 mL |

Stock solutions were prepared for glucose and $MgSO_4.7H_2O$ as solution A, CSL (corn steep liquor) as solution B, and the other ingredients as solution C. Then, the stock solutions A and C, as they were, were separately sterilized in an autoclave at 120° C. for 20 minutes. The pH of stock solution B was lowered to 2 by using sulfuric acid, and the solution was heated to 80° C. for 60 minutes, and then sterilized in an autoclave at 120° C. for 20 minutes. Then, the stock solutions A, B, and C were mixed, and ampicillin was added to the mixture at a final concentration of 100 m g/L to obtain the medium for seed culture.

Example 1: Production of Fibroin-Like Protein Under Glucose-Limited Condition 1

(1) Production of Fibroin-Like Protein Under Control Condition

According to the following procedures, the host bacterium was cultured using conventional typical culture conditions, namely, that the culture is performed as batch culture by using a starting medium containing an appropriate amount of glucose until the glucose in the culture medium is completely consumed. In this way, glucose is present in the culture medium in a sufficient amount with respect to the amount of glucose consumed by the host bacterium, in that all the glucose is consumed just before the end of the culture, which is immediately before the induction of the expression. In Example 1, these conditions are also referred to as "controlled conditions".

To 255 ml of the production medium (see Table 2) contained in a jar fermenter, 45 ml of the seed culture broth obtained in Reference Example 2 was inoculated. Culture was performed while maintaining the temperature of the culture medium at 37° C., aerating with 300 mL per 1 minute of air disinfected with a filter, stirring at 700 rpm, and maintaining the pH of the culture medium at a constant pH of 6.9 by appropriately blowing ammonia gas into the medium. During the culture, the culture medium was periodically sampled, and the glucose concentration in the culture medium was measured by using BF-5 (Oji Scientific Instruments). During the culture, the dissolved oxygen concentration in the culture medium was also measured by using a dissolved oxygen concentration sensor, OxyProbe (registered trademark) Dissolved Oxygen Sensors (Broadley-James), and was maintained at 20% of the saturated dissolved oxygen concentration. To maintain the dissolved oxygen concentration at 20% of the saturated concentration, the culture was stirred at a rate of up to 2000 rpm as required, and when the dissolved oxygen concentration was still too low even at this rate of stirring, the culture was also aerated with 30 mL per 1 minute of oxygen disinfected with a filter.

TABLE 2

Production medium
(per 1 L at the time of start of culture)

| | |
|---|---|
| Glucose | 45 g |
| $KH_2PO_4$ | 9 g |
| $MgSO_4 \cdot 7H_2O$ | 2.4 g |
| CSL | 1 g (as nitrogen amount) |
| $FeSO_4 \cdot 7H_2O$ | 40 mg |
| $MnSO_4 \cdot 5H_2O$ | 40 mg |
| $CaCl_2 \cdot 2H_2O$ | 40 mg |
| Isoleucine | 3 g |
| GD-113 (anti-foaming agent) | 0.1 mL |

Stock solutions were prepared for glucose and $MgSO_4 \cdot 7H_2O$ as solution A, CSL (corn steep liquor) as solution B, and the other ingredients as solution C. Then, the stock solutions A and C, as they were, were separately sterilized in an autoclave at 120° C. for 20 minutes. The pH of the stock solution B was lowered to 2 by using sulfuric acid, and the solution was heated to 80° C. for 60 minutes, and then sterilized in an autoclave at 120° C. for 20 minutes. Then, the stock solutions A, B, and C were mixed to obtain the production medium.

Glucose contained in the production medium was completely consumed at about 4 hours after the start of the culture. Immediately thereafter, 0.3 ml of the 1 M IPTG aqueous solution shown in Table 3 was added. Then, the culture temperature was set at 30° C., and the feed medium shown in Table 4 was added at a flow rate of 3.6 ml per 1 hour, and the culture was continued. The culture was aerated with 300 mL per 1 minute of air disinfected with a filter, and stirred at a rate of 700 rpm. During the culture, the dissolved oxygen concentration in the culture medium was measured by using a dissolved oxygen concentration sensor, OxyProbe (registered trademark) Dissolved Oxygen Sensors (Broadley-James), and was maintained at 20% of the saturated dissolved oxygen concentration. To maintain the dissolved oxygen concentration at 20% of the saturated concentration, the culture was stirred at a rate of up to 2000 rpm as required. The culture was continued while maintaining the pH of the culture medium at 6.9 by appropriately blowing ammonia gas into the culture medium.

TABLE 3

IPTG aqueous solution (per 1 L)

| | |
|---|---|
| IPTG (Nakalai Tesque) | 238.3 g |

The solution was sterilized in an autoclave at 120° C. for 20 minutes, and used.

TABLE 4

Feed medium (per 1 L)

| | |
|---|---|
| Glucose | 455 g |

The medium was sterilized in an autoclave at 120° C. for 20 minutes prior to use.

(2) Production of Fibroin-Like Protein Under Glucose-Limited Condition

According to the following procedures, the host bacterium was cultured while maintaining a low glucose concentration in the medium. In Example 1, this type of culture condition is also referred to as a "glucose-limited condition".

To 227 ml of the production medium shown in Table 5 contained in ajar fermenter, 45 ml of the seed culture broth obtained in Reference Example 2 was inoculated. Culture was performed while maintaining the temperature of the culture medium at 37° C., aerating with 300 mL per 1 minute of air disinfected with a filter, stirring at 700 rpm, and maintaining the pH of the culture medium at a constant 6.9 by appropriately blowing ammonia gas into the medium. During the culture, the culture medium was periodically sampled, and the glucose concentration in the culture medium was measured by using BF-5 (Oji Scientific Instruments). During the culture, dissolved oxygen concentration in the culture medium was also measured by using a dissolved oxygen concentration sensor, OxyProbe (registered trademark) Dissolved Oxygen Sensors (Broadley-James), and was maintained at 20% of the saturated dissolved oxygen concentration. To maintain the dissolved oxygen concentration at 20% of the saturated concentration, the culture was stirred at a rate of up to 2000 rpm as required, and when the dissolved oxygen concentration was still too low even when stirred at this increased rate, the culture was also aerated with 30 mL per 1 minute of oxygen disinfected with a filter.

TABLE 5

Production medium
(per 1 L at the time of start of culture)

| | |
|---|---|
| Glucose | 2 g |
| $KH_2PO_4$ | 9 g |
| $MgSO_4 \cdot 7H_2O$ | 2.4 g |
| CSL | 1 g (as nitrogen amount) |
| $FeSO_4 \cdot 7H_2O$ | 40 mg |
| $MnSO_4 \cdot 5H_2O$ | 40 mg |
| $CaCl_2 \cdot 2H_2O$ | 40 mg |
| Isoleucine | 3 g |
| GD-113 (anti-foaming agent) | 0.1 mL |

Stock solutions were prepared for glucose and $MgSO_4 \cdot 7H_2O$ as solution A, CSL (corn steep liquor) as solution B, and the other ingredients as solution C. Then, the stock solutions of A and C, as they were, were separately sterilized in an autoclave at 120° C. for 20 minutes. The pH of the stock solution B was lowered to 2 by using sulfuric acid, and the solution was heated at 80° C. for 60 minutes, and then sterilized in an autoclave at 120° C. for 20 minutes. Then, the stock solutions A, B, and C were mixed to obtain the production medium.

After the glucose in the production medium was completely consumed, the feed medium (Table 4) was added at a flow rate of 3.6 ml per 1 hour, and the culture was continued. The culture was aerated with 300 mL per 1 minute of air disinfected with a filter, and stirred at a rate of 700 rpm. During the culture, dissolved oxygen concentration in the culture medium was measured by using a dissolved oxygen concentration sensor, OxyProbe (registered trademark) Dissolved Oxygen Sensors (Broadley-James), and was maintained at 20% of the saturated dissolved oxygen concentration. To maintain the dissolved oxygen concentration at 20% of the saturated concentration, the culture was stirred at a rate up to 2000 rpm as required. The pH of the culture medium was controlled at a constant 6.9 by appropriately blowing ammonia gas into the culture medium.

The supply rate of glucose to the medium by the addition of the feed medium was lower than the consumption rate of glucose by the host bacterium, and the glucose concentration in the medium was consistently maintained at 0.5 g/L or lower from the start of the addition of the feed medium to the end of the culture.

After about 8 hours from the start of the culture, 0.3 ml of the 1 M IPTG aqueous solution shown in Table 3 was added. Then, the culture temperature was set at 30° C., the feed medium shown in Table 4 was added at a flow rate of 3.6 ml per 1 hour, and the culture was continued. The culture was aerated with 300 mL per 1 minute of air disinfected with a filter, and stirred at a rate of 700 rpm. During the culture, the dissolved oxygen concentration in the culture medium was measured by using a dissolved oxygen concentration sensor, OxyProbe (registered trademark) Dissolved Oxygen Sensors (Broadley-James), and was maintained at 20% of the saturated dissolved oxygen concentration. To maintain the dissolved oxygen concentration at 20% of the saturated concentration, the culture was stirred at a rate of up to 2000 rpm as required. The pH of the culture medium was controlled at a constant 6.9 by appropriately blowing ammonia gas into the culture medium.

(3) Analysis

In the culture described in sections (1) and (2) above, the culture medium was sampled in appropriate volumes during the culture and after the end of the culture, and subjected to the analysis described below.

OD620 of the culture medium was measured by the method described in Reference Example 2. The measurement results are shown in FIG. 1.

The glucose concentration in the culture medium was measured by using BF-5 (Oji Scientific Instruments). The measurement results are shown in FIG. 2.

The acetic acid concentration in the culture medium was measured by the following method. A culture supernatant separated from the culture medium was diluted 10 times with pure water, and analyzed by HPLC (Shimadzu) under the following conditions.

Column: Packed column Shim-pack SCR-102H×2 (serially connected)

Conditions: polarity, +; response, slow; gain, 0.1 µS/cm; range, 1; column temperature, 40° C.; mobile phase and reaction layer flow rate, 0.8 mL/minute The measurement results are shown in FIG. 3.

The concentrations of organic acids in the culture medium were measured by the following method at the start of the culture (common to the control condition and glucose-limited condition), and immediately after the addition of IPTG. The concentrations of the organic acids were measured in the same manner as that used for the aforementioned measurement of the acetic acid concentration. The measurement results are shown in FIG. 4. Under the glucose-limited condition, the concentrations of the organic acids at the time of the addition of IPTG were reduced to 0 to 50% of those observed under the control condition.

The produced fibroin-like protein was appropriately quantified. The amount of the fibroin-like protein produced is shown in FIG. 5 as the amount of accumulation relative to the volume of the culture medium, and in FIG. 6 as the amount of accumulation relative to cell weight. The cumulative productivity of the fibroin-like protein is shown in FIG. 7, and the cumulative specific production rate of the fibroin-like protein is shown in FIG. 8.

The accumulation amount of the fibroin-like protein relative to volume of the culture medium observed at 4 hours after the addition of IPTG was 0.27 g/L under the control condition, but it was 0.60 g/L under the glucose-limited condition. The accumulation amount of the fibroin-like protein relative to volume of the culture medium was 1.14 g/L at 13 hours after the addition of IPTG under the control condition, but it reached 1.24 g/L at 9 hours after the addition of IPTG under the glucose-limited condition.

The accumulation amount of the fibroin-like protein relative to cell weight observed at 4 hours after the addition of IPTG was 1.0% (w/w) under the control condition, but it was 2.5% (w/w) under the glucose-limited condition. The accumulation amount of the fibroin-like protein relative to cell weight was 3.8% (w/w) at 13 hours after the addition of IPTG under the control condition, but it reached 4.5% (w/w) at 9 hours after the addition of IPTG under the glucose-limited condition.

The cumulative productivity of the fibroin-like protein observed at 4 hours after the addition of IPTG was 0.07 g/L/h under the control condition, but it was 0.14 g/L/h under the glucose-limited condition. The cumulative productivity of the fibroin-like protein was 0.09 g/L/h at 13 hours after the addition of IPTG under the control condition, but it was maintained at 0.14 g/L/h even at 9 hours after the addition of IPTG under the glucose-limited condition. That is, under the glucose-limited condition, the maximum cumulative productivity of the fibroin-like protein after the addition of IPTG was improved by about 56% compared with that observed under the control condition (0.09 g/L/h→0.14 g/L/h).

The cumulative specific production rate of the fibroin-like protein observed at 4 hours after the addition of IPTG was 0.0020 g/g/h under the control condition, but it was 0.0033 g/g/h under the glucose-limited condition. The cumulative specific production rate of the fibroin-like protein was 0.0032 g/g/h at 13 hours after the addition of IPTG under the control condition, but it was 0.0042 g/g/h at 9 hours after the addition of IPTG under the glucose-limited condition.

On the basis of the results described above, it was revealed that by performing the culture under the glucose-limited condition, and then adding IPTG to induce the expression of the fibroin-like protein, the concentrations of the organic acids contained in the culture medium at the time of the addition of IPTG, that is, at the time of inducing the expression, were reduced, and production of the fibroin-like protein after the addition of IPTG was improved. Therefore, by reducing the accumulation amount(s) of organic acid(s) at the time of inducing the expression, production of the fibroin-like protein is improved.

Example 2: Production of Fibroin-Like Protein Under Glucose-Limited Condition 2

(1) Production of Fibroin-Like Protein Under Control Condition

According to the following procedures, the host bacterium was cultured using conventional typical culture conditions, namely, that the culture is performed as batch culture by using a starting medium containing an appropriate amount of glucose until the glucose in the culture medium is completely consumed. In this way, glucose is present in the culture medium in a sufficient amount with respect to the amount of glucose consumed by the host bacterium, in that all the glucose is consumed just before the end of the culture, which is immediately before the induction of the expression. In Example 2, this condition is also referred to as a "control condition".

By using the medium for seed culture shown in Table 6, culture was performed under the conditions described in Reference Example 2 until the glucose was completely consumed (12 hours) to obtain a seed culture broth. Then, to 255 ml of the production medium shown in Table 7 contained in a jar fermenter, 45 ml of the above seed culture broth was inoculated. Culture was performed while maintaining the temperature of the culture medium at 37° C., aerating with 300 mL per 1 minute of air disinfected with a filter, stirring at 700 rpm, and maintaining the pH of the culture medium at a constant 6.9 by appropriately blowing ammonia gas into the medium. During the culture, the culture medium was periodically sampled, and the glucose concentration in the culture medium was measured by using BF-5 (Oji Scientific Instruments). During the culture, the dissolved oxygen concentration in the culture medium was also measured by using a dissolved oxygen concentration sensor, OxyProbe (registered trademark) Dissolved Oxygen Sensors (Broadley-James), and was maintained at 20% of the saturated dissolved oxygen concentration. To maintain the dissolved oxygen concentration at 20% of the saturated concentration, the culture was stirred at a rate of up to 2000 rpm as required, and when the dissolved oxygen concentration was still too low even with the increased stirring rate, the culture was also aerated with 30 mL per 1 minute of oxygen disinfected with a filter.

TABLE 6

Medium for seed culture
(per 1 L at the time of start of culture)

| Glucose | 40 g |
|---|---|
| KH$_2$PO$_4$ | 2 g |
| MgSO$_4$·7H$_2$O | 1 g |
| Soybean hydrolysate | 1 g (as nitrogen amount) |
| FeSO$_4$·7H$_2$O | 10 mg |
| MnSO$_4$·5H$_2$O | 10 mg |
| Isoleucine | 0.8 g |
| GD-113 (anti-foaming agent) | 0.1 mL |

Stock solutions were prepared for glucose and MgSO$_4$.7H$_2$O as solution A, and the other ingredients as solution B. Then, the stock solution A, as it is, was sterilized in an autoclave at 120° C. for 20 minutes. The pH of the stock solution B was lowered to 2 with sulfuric acid, and the solution was heated at 80° C. for 60 minutes, and then sterilized in an autoclave at 120° C. for 20 minutes. Then, the stock solutions A and B were mixed, and ampicillin was added to the mixture at a final concentration of 100 m g/L to obtain the medium for seed culture.

TABLE 7

Production medium
(per 1 L at the time of start of culture)

| Glucose | 45 g |
|---|---|
| KH$_2$PO$_4$ | 5 g |
| MgSO$_4$·7H$_2$O | 2.4 g |
| CSL | 1 g (as nitrogen amount) |
| FeSO$_4$·7H$_2$O | 40 mg |
| MnSO$_4$·5H$_2$O | 40 mg |
| CaCl$_2$·2H$_2$O | 40 mg |
| Isoleucine | 1 g |
| GD-113 (anti-foaming agent) | 0.1 mL |

Stock solutions were prepared for glucose and MgSO$_4$.7H$_2$O as solution A, CSL (corn steep liquor) as solution B, and the other ingredients as solution C. Then, the stock solutions A and C, as they were, were separately sterilized in an autoclave at 120° C. for 20 minutes. The pH of the stock solution B was lowered to 2 with sulfuric acid, and the solution was heated to 80° C. for 60 minutes, and then sterilized in an autoclave at 120° C. for 20 minutes. Then, the stock solutions A, B, and C were mixed to obtain the production medium.

Glucose in the production medium was completely consumed at about 4 hours after the start of the culture. Immediately thereafter, 0.3 ml of the 1 M IPTG aqueous solution shown in Table 3 was added. Then, the culture temperature was set at 30° C., and the feed medium shown in Table 4 was added at a flow rate of 3.6 ml per 1 hour, and the culture was continued. The culture was aerated with 300 mL per 1 minute of air disinfected with a filter, and stirred at a rate of 700 rpm. During the culture, the dissolved oxygen concentration in the culture medium was measured by using a dissolved oxygen concentration sensor, OxyProbe (registered trademark) Dissolved Oxygen Sensors (Broadley-James), and was maintained at 20% of the saturated dissolved oxygen concentration. To maintain the dissolved oxygen concentration at 20% of the saturated concentration, the culture was stirred at a rate of up to 2000 rpm as required. The culture was continued while maintaining the pH of the culture medium at a constant 6.9 by appropriately blowing ammonia gas into the culture medium.

(2) Production of Fibroin-Like Protein Under Glucose-Limited Condition

The results obtained in Example 1 under the glucose-limited condition were used as results of Example 2 obtained under the glucose-limited condition.

(3) Analysis

In the culture described in sections (1) and (2) above, the culture medium was sampled in appropriate volumes during the culture and after the end of the culture, and subjected to the analysis described below.

OD620 of the culture medium was measured by the method described in Reference Example 2. The measurement results are shown in FIG. 9.

The glucose concentration in the culture medium was measured by using BF-5 (Oji Scientific Instruments). The measurement results are shown in FIG. 10.

The acetic acid concentration in the culture medium was measured by the following method. A culture supernatant separated from the culture medium was diluted 10 times with pure water, and analyzed by HPLC (Shimadzu) under the following conditions.

Column: Packed column Shim-pack SCR-102H×2 (serially connected)

Condition: polarity, +; response, slow; gain, 0.1 µS/cm; range, 1; column temperature, 40° C.; mobile phase and reaction layer flow rate, 0.8 mL/minute The measurement results are shown in FIG. 11.

The concentrations of organic acids in the culture medium were measured by the following method at the start of the culture and immediately after the addition of IPTG. The concentrations of the organic acids were measured in the same manner as that used for the aforementioned measurement of the acetic acid concentration. The measurement results are shown in FIG. 12. Under the glucose-limited condition, the concentrations of the organic acids at the time of the addition of IPTG were reduced to 0 to 50% of those observed under the control condition.

The produced fibroin-like protein was appropriately quantified. The amount of the fibroin-like protein produced is shown in FIG. 13 as the amount of accumulation relative to volume of the culture medium, and FIG. 14 as the amount of accumulation relative to cell weight. The cumulative productivity of the fibroin-like protein is shown in FIG. 15, and the cumulative specific production rate of the fibroin-like protein is shown in FIG. 16.

The accumulation amount of the fibroin-like protein relative to volume of the culture medium was 0.25 g/L at 5 hours after the addition of IPTG under the control condition, but it was 0.60 g/L at 4 hours after the addition of IPTG under the glucose-limited condition. The accumulation amount of the fibroin-like protein relative to volume of the culture medium was 0.85 g/L at 20 hours after the addition of IPTG under the control condition, but it reached 1.24 g/L at 9 hours after the addition of IPTG under the glucose-limited condition.

The accumulation amount of the fibroin-like protein relative to cell weight was 1.1% (w/w) at 5 hours after the addition of IPTG under the control condition, but it was 2.5% (w/w) at 4 hours after the addition of IPTG under the glucose-limited condition. The accumulation amount of the fibroin-like protein relative to cell weight was 3.0% (w/w) at 20 hours after the addition of IPTG under the control condition, but it reached 4.5% (w/w) at 9 hours after the addition of IPTG under the glucose-limited condition.

The cumulative productivity of the fibroin-like protein was 0.05 g/L/h at 5 hours after the addition of IPTG under the control condition, but it was 0.14 g/L/h at 4 hours after the addition of IPTG under the glucose-limited condition. The cumulative productivity of the fibroin-like protein was 0.05 g/L/h at 20 hours after the addition of IPTG under the control condition, but it was maintained at 0.14 g/L/h even at 9 hours after the addition of IPTG under the glucose-limited condition. That is, under the glucose-limited condition, the maximum cumulative productivity of the fibroin-like protein after the addition of IPTG was improved by about 180% compared with that observed under the control condition (0.05 g/L/h→0.14 g/L/h).

The cumulative specific production rate of the fibroin-like protein was 0.0018 g/g/h at 5 hours after the addition of IPTG under the control condition, but it was 0.0033 g/g/h at 4 hours after the addition of IPTG under the glucose-limited condition. The cumulative specific production rate of the fibroin-like protein was 0.0018 g/g/h at 20 hours after the addition of IPTG under the control condition, but it was 0.0042 g/g/h at 9 hours after the addition of IPTG under the glucose-limited condition.

On the basis of the results described above, it was revealed that by performing the culture under the glucose-limited condition, and then adding IPTG to induce the expression of the fibroin-like protein, the concentrations of organic acids in the culture medium at the time of the addition of IPTG, that is, at the time of inducing the expression, were reduced, and production of the fibroin-like protein after the addition of IPTG was improved. Therefore, by reducing the accumulation amount(s) of organic acid(s) at the time of inducing the expression, production of the fibroin-like protein is improved.

Furthermore, in comparison of the results obtained under the control condition of Example 1 and the control condition of Example 2, the concentrations of organic acids such as acetic acid contained in the culture medium at the time of the addition of IPTG (at the time of inducing the expression) were more reduced, and production of the fibroin-like protein after the addition of IPTG was improved under the control condition of Example 1 compared with those observed under the control condition of Example 2. This fact also suggests that by reducing the accumulation amount(s) of organic acid(s) at the time of inducing the expression, production of the fibroin-like protein is improved.

Example 3: Production of Wild-Type ADF3 Under Glucose-Limited Condition

Construction of Wild-Type ADF3-Producing Bacterium

In this example, ADF3 of *Araneus diadematus* having a His tag and the HRV3C protease recognition sequence added to the N-terminus was produced as a fibroin-like protein. In this example, this fusion protein is also referred to simply as "wild-type ADF3".

A DNA encoding the wild-type ADF3 was introduced into pET22b(+) at the NdeI-EcoRI site by using the In-Fusion kit to obtain an expression plasmid for the wild-type ADF3, pET22b-ADF3WT. *Escherichia coli* BLR(DE3) was transformed with pET22b-ADF3WT to obtain a wild-type ADF3-producing bacterium, BLR(DE3)/pET22b-ADF3WT. The nucleotide sequence of the coding region of wild-type ADF3 and surrounding sequences thereof in pET22b-ADF3WT are shown as SEQ ID NO: 4. The sequence of the positions 12 to 1994 in the sequence of SEQ ID NO: 4 corresponds to the coding region of the wild-type ADF3. The amino acid sequence of the wild-type ADF3 encoded by pET22b-ADF3WT is shown as SEQ ID NO: 5.

(B) Production of Wild-Type ADF3

Production of Wild-Type ADF3 Under Control Condition

Culture was performed under the following condition. In Example 3, this condition is also referred to as "control condition".

By using the medium for seed culture shown in Table 1, culture was performed under the condition described in Reference Example 2 until glucose was completely consumed to obtain a seed culture broth. Then, to 255 ml of the production medium shown in Table 2 in a jar fermenter, 45 ml of the above seed culture broth was inoculated. Culture was performed while maintaining the temperature of the culture medium at 37° C., aerating with 300 mL per 1 minute of air disinfected with a filter, stirring at 700 rpm, and maintaining the pH of the culture medium at a constant 6.9 by appropriately blowing ammonia gas into the medium. During the culture, the culture medium was periodically sampled, and the glucose concentration in the culture medium was measured by using BF-5 (Oji Scientific Instruments). During the culture, the dissolved oxygen concentration in the culture medium was also measured by using a dissolved oxygen concentration sensor, OxyProbe (registered trademark) Dissolved Oxygen Sensors (Broadley-James), and was maintained at 20% of the saturated dissolved oxygen concentration. To maintain the dissolved oxygen concentration at 20% of the saturated concentration, the culture was stirred at a rate of up to 2000 rpm as required, and when the dissolved oxygen concentration was still too low even with the increased rate of stirring, the culture was also aerated with 30 mL per 1 minute of oxygen disinfected with a filter.

Glucose in the production medium was completely consumed at about 4.0 hours after the start of the culture. Immediately thereafter, 0.3 ml of the 1 M IPTG aqueous solution shown in Table 3 was added. Then, the culture temperature was maintained at 30° C., and the feed medium shown in Table 8 was added at a flow rate of 2.6 ml per 1 hour, and the culture was continued. The culture was aerated with 300 mL per 1 minute of air disinfected with a filter, and stirred at a rate of 700 rpm. During the culture, the dissolved oxygen concentration in the culture medium was measured by using a dissolved oxygen concentration sensor, OxyProbe (registered trademark) Dissolved Oxygen Sensors (Broadley-James), and was maintained at 20% of the saturated dissolved oxygen concentration. To maintain the dissolved oxygen concentration at 20% of the saturated concentration, the culture was stirred at a rate of up to 2000 rpm as required. The pH of the culture medium was controlled to a constant 6.9 by appropriately blowing ammonia gas into the culture medium.

TABLE 8

Feed medium (per 1 L)

| Glucose | 700 g |
|---|---|

The medium was sterilized in an autoclave at 120° C. for 20 minutes.

(2) Production of Wild-Type ADF3 Under Glucose-Limited Condition

According to the following procedures, the host bacterium was cultured while maintaining a low glucose concentration in the medium at the time of proliferation of the bacterium before the induction of the expression. In Example 3, this is also referred to as a "glucose-limited condition".

By using the medium for seed culture shown in Table 1, culture was performed under the condition described in Reference Example 2 until glucose was completely consumed to obtain a seed culture broth. Then, to 255 ml of the production medium shown in Table 2 in a jar fermenter, 45 ml of the above seed culture broth was inoculated. Culture was performed while maintaining the temperature of the culture medium at 37° C., aerating with 300 mL per 1 minute of air disinfected with a filter, stirring at 700 rpm, and maintaining the pH of the culture medium at a constant 6.9 by appropriately blowing ammonia gas into the medium. During the culture, the culture medium was periodically sampled, and the glucose concentration in the culture medium was measured by using BF-5 (Oji Scientific Instruments). During the culture, the dissolved oxygen concentration in the culture medium was also measured by using a dissolved oxygen concentration sensor, OxyProbe (registered trademark) Dissolved Oxygen Sensors (Broadley-James), and was maintained at 20% of the saturated dissolved oxygen concentration. To maintain the dissolved oxygen concentration at 20% of the saturated concentration, the culture was stirred at a rate of up to 2000 rpm as required, and when the dissolved oxygen concentration was still too low even when stirred at this increased rate, the culture was aerated with 30 mL per 1 minute of oxygen disinfected with a filter.

Glucose in the production medium was completely consumed at about 4.0 hours after the start of the culture. Immediately thereafter, the feed medium shown in Table 8 was added at a flow rate of 14.6 ml per 1 hour, and the culture was continued. The culture was aerated with 300 mL per 1 minute of air disinfected with a filter, and stirred at a rate of 700 rpm. During the culture, the dissolved oxygen concentration in the culture medium was measured by using a dissolved oxygen concentration sensor, OxyProbe (registered trademark) Dissolved Oxygen Sensors (Broadley-James), and was maintained at 20% of the saturated dissolved oxygen concentration. To maintain the dissolved oxygen concentration at 20% of the saturated concentration, the culture was stirred at a rate of up to 2000 rpm as required, and when the dissolved oxygen concentration was still too low even with the increased rate of stirring, the culture was aerated with 30 to 90 mL per 1 minute of oxygen disinfected with a filter. When it became difficult to maintain the dissolved oxygen concentration, the flow rate of the feed medium was decreased. The pH of the culture medium was controlled at a constant 6.9 by appropriately blowing ammonia gas into the culture medium.

After about 8 hours from the start of the culture, that is, at the time point when the volume of the feed medium shown in Table 8 reached 58 mL, 1.1 ml of the 1 M IPTG aqueous solution shown in Table 3 was added. Then, the culture temperature was set at 30° C., and the feed medium shown in Table 8 was added at a flow rate of 2.6 ml per 1 hour, and the culture was continued. The culture was aerated with 300 mL per 1 minute of air disinfected with a filter, and the culture was stirred at a rate of 700 rpm. During the culture, the dissolved oxygen concentration in the culture medium was measured by using a dissolved oxygen concentration sensor, OxyProbe (registered trademark) Dissolved Oxygen Sensors (Broadley-James), and was maintained at 20% of the saturated dissolved oxygen concentration. To maintain the dissolved oxygen concentration at 20% of the saturated concentration, the culture was stirred at a rate of up to 2000 rpm as required. The pH of the culture medium was controlled at a constant 6.9 by appropriately blowing ammonia gas into the culture medium.

(3) Analysis

In the culture described in sections (1) and (2) above, the culture medium was sampled in appropriate volumes during the culture and after the end of the culture, and subjected to the analysis described below.

OD620 of the culture medium was measured by the method described in Reference Example 2. The measurement results are shown in FIG. 17.

The glucose concentration in the culture medium was measured by using BF-5 (Oji Scientific Instruments). The measurement results are shown in FIG. 18.

The acetic acid concentration in the culture medium was measured by the following method. A culture supernatant separated from the culture medium was diluted 10 times with pure water, and analyzed by HPLC (Shimadzu) under the following conditions.

Column: Packed column Shim-pack SCR-102H×2 (serially connected)

Conditions: polarity, +; response, slow; gain, 0.1 µS/cm; range, 1; column temperature, 40° C.; mobile phase and reaction layer flow rate, 0.8 mL/minute The measurement results are shown in FIG. 19 and Table 9. Under the glucose-limited condition, the acetic acid concentration at the time of the addition of IPTG was reduced.

The concentrations of organic acids in the culture medium were measured by the following method at the start of the culture, similar to the control condition and glucose-limited condition, and immediately after the addition of IPTG. The concentrations of the organic acids were measured in the same manner as that for the aforementioned measurement of the acetic acid concentration. The measurement results are shown in FIG. 20. Under the glucose-limited condition, the concentrations of the organic acids at the time of the addition of IPTG were reduced to 7 to 15% of those observed under the control condition.

The produced wild-type ADF3 was appropriately quantified. The data concerning the production amount of the wild-type ADF3 (accumulation amount of wild-type ADF3 relative to volume of the culture medium, accumulation amount of wild-type ADF3 relative to cell weight, and cumulative productivity of wild-type ADF3) are shown in FIG. 21A to 21C, respectively, and Table 9.

The accumulation amount of the wild-type ADF3 relative to volume of the culture medium was 0.022 g/L at 42 hours after the addition of IPTG under the control condition, but it was improved to 0.055 g/L at 38 hours after the addition of IPTG under the glucose-limited condition. The accumulation amount of the wild-type ADF3 relative to cell weight was 0.055% at 42 hours after the addition of IPTG under the control condition, but it was improved to 0.100% at 38 hours after the addition of IPTG under the glucose-limited condition. The cumulative productivity of the wild-type ADF3 was 0.00058 g/L/h at 42 hours after the addition of IPTG under the control condition, but it was improved to 0.0016 g/L/h at 38 hours after the addition of IPTG under the glucose-limited condition.

On the basis of the results described above, it was revealed that by performing the culture under the glucose-limited condition, and then adding IPTG to induce the expression of the wild-type ADF3, the concentrations of organic acids in the culture medium at the time of addition of IPTG, that is, at the time of inducing the expression, were reduced, and production of the wild-type ADF3 after the addition of IPTG was improved. Therefore, by reducing the accumulation amount(s) of organic acid(s) at the time of inducing the expression, production of the wild-type ADF3 is improved.

TABLE 9

|  | Control (●); at 42 hours after addition of IPTG | Glucose limitation (Δ); at 38 hours after addition of IPTG |
| --- | --- | --- |
| ADF3 as BSA (g/L) | 0.022 | 0.055 |

TABLE 9-continued

|  | Control (●); at 42 hours after addition of IPTG | Glucose limitation (Δ); at 38 hours after addition of IPTG |
| --- | --- | --- |
| ADF3/Cell as BSA (%-w/w) | 0.055 | 0.100 |
| Cumulative productivity of ADF3 (g/L/h) | 0.00058 | 0.0016 |
| Acetate (g/L, at the time of induction) | 1.040 | 0.160 |

INDUSTRIAL APPLICABILITY

According to the present invention, proteins such as fibroin-like protein can be efficiently produced.

EXPLANATION OF SEQUENCE LISTING

SEQ ID NO: 1: Nucleotide sequence of fibroin-like protein gene used in Examples 1 and 2

SEQ ID NO: 2: Amino acid sequence of protein encoded by the fibroin-like protein gene used in Examples 1 and 2

SEQ ID NO: 3: Amino acid sequence of ADF3 protein (partial) of *Araneus diadematus*

SEQ ID NO: 4: Nucleotide sequence of coding region of wild-type ADF3 and surrounding sequences thereof in pET22b-ADF3WT SEQ ID NO: 5: Amino acid sequence of wild-type ADF3 encoded by pET22b-ADF3WT

The invention claimed is:

1. A method for producing a fibroin-like protein, the method comprising:
   (A) culturing an *Escherichia coli* bacterium having a gene encoding the fibroin-like protein in a medium,
   (B) inducing expression of the gene encoding the fibroin-like protein while reducing accumulation of an organic acid, and
   (C) collecting the fibroin-like protein;
   wherein said reducing accumulation of the organic acid is initiated by limiting a carbon source in the medium before inducing the expression, and
   wherein the organic acid is selected from the group consisting of acetic acid, citric acid, succinic acid, formic acid, and combinations thereof.

2. The method according to claim 1, wherein the amount of the organic acid accumulated in the medium during step (B) is 4.5 g/L or less.

3. The method according to claim 1, wherein the amount of the organic acid, accumulated in the medium during step (B) is 4.0 g/L or less, and wherein said organic acid is acetic acid.

4. The method according to claim 1, wherein concentration of the carbon source in the medium is 0.5 g/L or lower.

5. The method according to claim 1, wherein the carbon source is glucose.

6. The method according to claim 1, wherein said reducing accumulation of the organic acid is further achieved by modifying the *Escherichia coli* bacterium so that an ability to produce the organic acid is reduced.

7. The method according to claim 1, wherein said organic acid is acetic acid.

* * * * *

SEQUENCE LISTING

```
<160> NUMBER OF SEQ ID NOS: 5

<210> SEQ ID NO 1
<211> LENGTH: 3465
<212> TYPE: DNA
<213> ORGANISM: Artificial Sequence
<220> FEATURE:
<223> OTHER INFORMATION: fibroin-like protein gene
<220> FEATURE:
<221> NAME/KEY: CDS
<222> LOCATION: (1)..(3465)

<400> SEQUENCE: 1 atg cat cac cat cat cat cat cac cac cac cat tcc tcg ggc tca tcc       48
Met His His His His His His His His His Ser Ser Gly Ser Ser
1               5                   10                  15 ttg gaa gtg tta ttt caa gga cca gca cga gcc ggt tcg gga caa caa       96
Leu Glu Val Leu Phe Gln Gly Pro Ala Arg Ala Gly Ser Gly Gln Gln
                20                  25                  30 ggg cct ggc cag cag ggc cca ggt caa caa ggg cca gga cag cag ggt      144
Gly Pro Gly Gln Gln Gly Pro Gly Gln Gln Gly Pro Gly Gln Gln Gly
            35                  40                  45 cct tat ggg ccc ggc gca agc gca gca gct gcg gcc gct ggt ggc tat      192
Pro Tyr Gly Pro Gly Ala Ser Ala Ala Ala Ala Ala Ala Gly Gly Tyr
        50                  55                  60 ggt cct ggc tcc ggt caa cag ggc cct tcg caa caa ggt ccc ggg cag      240
Gly Pro Gly Ser Gly Gln Gln Gly Pro Ser Gln Gln Gly Pro Gly Gln
65                  70                  75                  80 caa ggt cct ggt ggc cag ggt ccc tac ggg ccg ggg gcg agt gcg gca      288
Gln Gly Pro Gly Gly Gln Gly Pro Tyr Gly Pro Gly Ala Ser Ala Ala
```

-continued

|  |  |  | 85 |  |  |  | 90 |  |  |  | 95 |  |  |  |
|---|---|---|---|---|---|---|---|---|---|---|---|---|---|---|
| gca | gcc | gct | gca | ggc | ggt | tat | ggt | cca | gga | agc | gga | cag | caa | ggt ccg | 336 |
| Ala | Ala | Ala | Ala | Gly | Gly | Tyr | Gly | Pro | Gly | Ser | Gly | Gln | Gln | Gly Pro |
|  |  |  | 100 |  |  |  | 105 |  |  |  | 110 |  |  |  |

```
gca gcc gct gca ggc ggt tat ggt cca gga agc gga cag caa ggt ccg    336
Ala Ala Ala Ala Gly Gly Tyr Gly Pro Gly Ser Gly Gln Gln Gly Pro
            100                 105                 110 gga ggt caa ggt ccg tat ggc cca ggc tct agc gcg gct gcc gct gcc    384
Gly Gly Gln Gly Pro Tyr Gly Pro Gly Ser Ser Ala Ala Ala Ala Ala
            115                 120                 125 gcg ggt ggc aac gga cca ggg agc gga caa cag ggc gcg gga caa cag    432
Ala Gly Gly Asn Gly Pro Gly Ser Gly Gln Gln Gly Ala Gly Gln Gln
            130                 135                 140 ggt cca gga cag caa ggc cca ggg gcg tcg gcg gct gca gcg gcg gcc    480
Gly Pro Gly Gln Gln Gly Pro Gly Ala Ser Ala Ala Ala Ala Ala Ala
145                 150                 155                 160 gga ggc tat gga ccc ggc tca gga caa cag gga ccg ggt caa caa gga    528
Gly Gly Tyr Gly Pro Gly Ser Gly Gln Gln Gly Pro Gly Gln Gln Gly
                165                 170                 175 ccc ggt ggc caa ggc ccc tat ggc ccg ggc gcc agc gcg gcc gca gcc    576
Pro Gly Gly Gln Gly Pro Tyr Gly Pro Gly Ala Ser Ala Ala Ala Ala
                180                 185                 190 gcc gcg ggc ggg tac ggc ccc ggt agc ggc cag gga cca ggt cag cag    624
Ala Ala Gly Gly Tyr Gly Pro Gly Ser Gly Gln Gly Pro Gly Gln Gln
                195                 200                 205 ggg cca gga ggt cag ggc cca tac ggt ccg ggc gca tcc gcg gcg gcg    672
Gly Pro Gly Gly Gln Gly Pro Tyr Gly Pro Gly Ala Ser Ala Ala Ala
            210                 215                 220 gca gcg gca ggt ggc tac ggt ccc gga agc ggc caa cag ggg cca ggg    720
Ala Ala Ala Gly Gly Tyr Gly Pro Gly Ser Gly Gln Gln Gly Pro Gly
225                 230                 235                 240 caa caa gga cca gga caa caa ggt cct ggg ggc caa gga ccg tat gga    768
Gln Gln Gly Pro Gly Gln Gln Gly Pro Gly Gly Gln Gly Pro Tyr Gly
                245                 250                 255 cca gga gca tca gct gca gcc gcg gca gct ggc ggt tac ggt cca ggc    816
Pro Gly Ala Ser Ala Ala Ala Ala Ala Ala Gly Gly Tyr Gly Pro Gly
                260                 265                 270 tac ggc cag cag ggt ccg ggt cag cag gga ccg gga ggc cag ggg cct    864
Tyr Gly Gln Gln Gly Pro Gly Gln Gln Gly Pro Gly Gly Gln Gly Pro
                275                 280                 285 tat ggc cct ggc gct tcc gca gcc agt gcc gct tct gga gga tac ggg    912
Tyr Gly Pro Gly Ala Ser Ala Ala Ser Ala Ala Ser Gly Gly Tyr Gly
            290                 295                 300 ccg gga agc ggt cag caa ggc cct ggc caa caa gga cct gga ggc caa    960
Pro Gly Ser Gly Gln Gln Gly Pro Gly Gln Gln Gly Pro Gly Gly Gln
305                 310                 315                 320 ggg ccc tac ggc cca gga gcc tcg gca gcc gca gct gcc gca ggt ggg   1008
Gly Pro Tyr Gly Pro Gly Ala Ser Ala Ala Ala Ala Ala Ala Gly Gly
                325                 330                 335 tat ggg cca ggt agc ggg caa caa ggg ccg ggt cag caa gga ccg ggg   1056
Tyr Gly Pro Gly Ser Gly Gln Gln Gly Pro Gly Gln Gln Gly Pro Gly
                340                 345                 350 caa cag gga cct ggg cag caa gga ccc ggg ggt caa ggc ccg tac gga   1104
Gln Gln Gly Pro Gly Gln Gln Gly Pro Gly Gly Gln Gly Pro Tyr Gly
            355                 360                 365 cct ggt gcg tct gca gct gct gct gcg gct ggt gga tat ggt ccg gga   1152
Pro Gly Ala Ser Ala Ala Ala Ala Ala Ala Gly Gly Tyr Gly Pro Gly
370                 375                 380 tcg ggg cag cag ggt ccc ggt cag cag ggc cct ggt cag cag ggg cca   1200
Ser Gly Gln Gln Gly Pro Gly Gln Gln Gly Pro Gly Gln Gln Gly Pro
385                 390                 395                 400 ggc caa cag gga ccc gga caa caa ggc ccg ggt caa cag ggt cct gga   1248
```

```
Gly Gln Gln Gly Pro Gly Gln Gln Gly Pro Gly Gln Gln Gly Pro Gly
                405                 410                 415 cag cag ggg ccg ggc caa caa ggc cct ggg caa cag ggt ccg ggg gga      1296
Gln Gln Gly Pro Gly Gln Gln Gly Pro Gly Gln Gln Gly Pro Gly Gly
            420                 425                 430 cag ggg gcc tat ggg cct ggc gca tct gcc gcc gct ggc gca gcc ggt      1344
Gln Gly Ala Tyr Gly Pro Gly Ala Ser Ala Ala Ala Gly Ala Ala Gly
        435                 440                 445 ggg tac ggg cct ggg tca ggt caa cag ggg cct ggt caa caa ggc ccc      1392
Gly Tyr Gly Pro Gly Ser Gly Gln Gln Gly Pro Gly Gln Gln Gly Pro
    450                 455                 460 ggg caa cag ggc ccc ggc cag caa ggt cca ggg cag cag ggc ccg gga      1440
Gly Gln Gln Gly Pro Gly Gln Gln Gly Pro Gly Gln Gln Gly Pro Gly
465                 470                 475                 480 cag caa ggg cct gga caa cag ggg ccc gga cag cag gga cct tac ggg      1488
Gln Gln Gly Pro Gly Gln Gln Gly Pro Gly Gln Gln Gly Pro Tyr Gly
                485                 490                 495 ccc ggt gcg agc gca gcg gcc gcc gca ggg gga tat ggc ccc gga          1536
Pro Gly Ala Ser Ala Ala Ala Ala Ala Gly Gly Tyr Gly Pro Gly
            500                 505                 510 tcg ggc cag cag gga cca ggc cag caa gga cct ggc caa cag ggc ccg      1584
Ser Gly Gln Gln Gly Pro Gly Gln Gln Gly Pro Gly Gln Gln Gly Pro
        515                 520                 525 ggg ggt cag ggg ccg tat ggt ccc ggc gct gca agt gct gca gtg tcc      1632
Gly Gly Gln Gly Pro Tyr Gly Pro Gly Ala Ala Ser Ala Ala Val Ser
    530                 535                 540 gtt tct aga gca cga gcc ggt tcg gga caa caa ggg cct ggc cag cag      1680
Val Ser Arg Ala Arg Ala Gly Ser Gly Gln Gln Gly Pro Gly Gln Gln
545                 550                 555                 560 ggc cca ggt caa caa ggg cca gga cag cag ggt cct tat ggg ccc ggc      1728
Gly Pro Gly Gln Gln Gly Pro Gly Gln Gln Gly Pro Tyr Gly Pro Gly
                565                 570                 575 gca agc gca gca gct gcg gcc gct ggt ggc tat ggt cct ggc tcc ggt      1776
Ala Ser Ala Ala Ala Ala Ala Gly Gly Tyr Gly Pro Gly Ser Gly
            580                 585                 590 caa cag ggc cct tcg caa caa ggt ccc ggg cag caa ggt cct ggt ggc      1824
Gln Gln Gly Pro Ser Gln Gln Gly Pro Gly Gln Gln Gly Pro Gly Gly
        595                 600                 605 cag ggt ccc tac ggg ccg ggg gcg agt gcg gca gca gcc gct gca ggc      1872
Gln Gly Pro Tyr Gly Pro Gly Ala Ser Ala Ala Ala Ala Ala Gly
    610                 615                 620 ggt tat ggt cca gga agc gga cag caa ggt ccg gga ggt caa ggt ccg      1920
Gly Tyr Gly Pro Gly Ser Gly Gln Gln Gly Pro Gly Gly Gln Gly Pro
625                 630                 635                 640 tat ggc cca ggc tct agc gcg gct gcc gct gcc gcg ggt ggc aac gga      1968
Tyr Gly Pro Gly Ser Ser Ala Ala Ala Ala Ala Gly Gly Asn Gly
                645                 650                 655 cca ggg agc gga caa cag ggc gcg gga caa cag ggt cca gga cag caa      2016
Pro Gly Ser Gly Gln Gln Gly Ala Gly Gln Gln Gly Pro Gly Gln Gln
            660                 665                 670 ggc cca ggg gcg tcg gcg gct gca gcg gcg gcc gga ggc tat gga ccc      2064
Gly Pro Gly Ala Ser Ala Ala Ala Ala Ala Ala Gly Gly Tyr Gly Pro
        675                 680                 685 ggc tca gga caa cag gga ccg ggt caa caa gga ccc ggt ggc caa ggc      2112
Gly Ser Gly Gln Gln Gly Pro Gly Gln Gln Gly Pro Gly Gly Gln Gly
    690                 695                 700 ccc tat ggc ccg ggc gcc agc gcg gcc gca gcc gcc gcg ggc ggg tac      2160
Pro Tyr Gly Pro Gly Ala Ser Ala Ala Ala Ala Ala Ala Gly Gly Tyr
705                 710                 715                 720
```

-continued

```
ggc ccc ggt agc ggc cag gga cca ggt cag cag ggg cca gga ggt cag      2208
Gly Pro Gly Ser Gly Gln Gly Pro Gly Gln Gln Gly Pro Gly Gly Gln
            725                 730                 735 ggc cca tac ggt ccg ggc gca tcc gcg gcg gcg gca gcg gca ggt ggc      2256
Gly Pro Tyr Gly Pro Gly Ala Ser Ala Ala Ala Ala Ala Ala Gly Gly
            740                 745                 750 tac ggt ccc gga agc ggc caa cag ggg cca ggg caa caa gga cca gga      2304
Tyr Gly Pro Gly Ser Gly Gln Gln Gly Pro Gly Gln Gln Gly Pro Gly
            755                 760                 765 caa caa ggt cct ggg ggc caa gga ccg tat gga cca gga gca tca gct      2352
Gln Gln Gly Pro Gly Gly Gln Gly Pro Tyr Gly Pro Gly Ala Ser Ala
            770                 775                 780 gca gcc gcg gca gct ggt ggt tac ggt cca ggc tac ggc cag cag ggt      2400
Ala Ala Ala Ala Ala Gly Gly Tyr Gly Pro Gly Tyr Gly Gln Gln Gly
785                 790                 795                 800 ccg ggt cag cag gga ccg gga ggc cag ggg cct tat ggc cct ggc gct      2448
Pro Gly Gln Gln Gly Pro Gly Gly Gln Gly Pro Tyr Gly Pro Gly Ala
                805                 810                 815 tcc gca gcc agt gcc gct tct gga gga tac ggg ccg gga agc ggt cag      2496
Ser Ala Ala Ser Ala Ala Ser Gly Gly Tyr Gly Pro Gly Ser Gly Gln
                820                 825                 830 caa ggc cct ggc caa caa gga cct gga ggc caa ggg ccc tac ggc cca      2544
Gln Gly Pro Gly Gln Gln Gly Pro Gly Gly Gln Gly Pro Tyr Gly Pro
                835                 840                 845 gga gcc tcg gca gcc gca gct gcc gca ggt ggg tat ggg cca ggt agc      2592
Gly Ala Ser Ala Ala Ala Ala Ala Gly Gly Tyr Gly Pro Gly Ser
850                 855                 860 ggg caa caa ggg ccg ggt cag caa gga ccg ggg caa cag gga cct ggg      2640
Gly Gln Gln Gly Pro Gly Gln Gln Gly Pro Gly Gln Gln Gly Pro Gly
865                 870                 875                 880 cag caa gga ccc ggg ggt caa ggc ccg tac gga cct ggt gcg tct gca      2688
Gln Gln Gly Pro Gly Gly Gln Gly Pro Tyr Gly Pro Gly Ala Ser Ala
                885                 890                 895 gct gct gct gcg gct ggt gga tat ggt ccg gga tcg ggg cag cag ggt      2736
Ala Ala Ala Ala Ala Gly Gly Tyr Gly Pro Gly Ser Gly Gln Gln Gly
                900                 905                 910 ccc ggt cag cag ggc cct ggt cag caa ggg cca ggc caa cag gga ccc      2784
Pro Gly Gln Gln Gly Pro Gly Gln Gln Gly Pro Gly Gln Gln Gly Pro
                915                 920                 925 gga caa caa ggc ccg ggt caa cag ggt cct gga cag cag ggg ccg ggc      2832
Gly Gln Gln Gly Pro Gly Gln Gln Gly Pro Gly Gln Gln Gly Pro Gly
            930                 935                 940 caa caa ggc cct ggg caa cag ggt ccg ggg gga cag ggg gcc tat ggg      2880
Gln Gln Gly Pro Gly Gln Gln Gly Pro Gly Gly Gln Gly Ala Tyr Gly
945                 950                 955                 960 cct ggc gca tct gcc gcc gct ggc gca gcc ggt ggg tac ggg cct ggg      2928
Pro Gly Ala Ser Ala Ala Ala Gly Ala Ala Gly Gly Tyr Gly Pro Gly
                965                 970                 975 tca ggt caa cag ggg cct ggt caa caa ggc ccc ggg caa cag ggc ccc      2976
Ser Gly Gln Gln Gly Pro Gly Gln Gln Gly Pro Gly Gln Gln Gly Pro
            980                 985                 990 ggc cag caa ggt cca ggg cag cag  ggc ccg gga cag caa  ggg cct gga    3024
Gly Gln Gln Gly Pro Gly Gln Gln  Gly Pro Gly Gln Gln  Gly Pro Gly
            995                 1000                1005 caa cag  ggg ccc gga cag cag  gga cct tac ggg ccc  ggt gcg agc       3069
Gln Gln  Gly Pro Gly Gln Gln  Gly Pro Tyr Gly Pro  Gly Ala Ser
        1010                1015                 1020 gca gcg gcc gcc gcc gca ggg  gga tat ggc ccc gga  tcg ggc cag        3114
Ala Ala Ala Ala Ala Ala Gly  Gly Tyr Gly Pro Gly  Ser Gly Gln
        1025                1030                 1035
```

```
cag gga cca ggc cag caa gga cct ggc caa cag ggc ccg ggg ggt     3159
Gln Gly Pro Gly Gln Gln Gly Pro Gly Gln Gln Gly Pro Gly Gly
        1040                1045                1050 cag ggg ccg tat ggt ccc ggc gct gca agt gct gca gtg tcc gtt     3204
Gln Gly Pro Tyr Gly Pro Gly Ala Ala Ser Ala Ala Val Ser Val
1055                1060                1065 gga ggt tac ggc cct cag tct tcg tct gtt ccg gtg gcg tcc gca     3249
Gly Gly Tyr Gly Pro Gln Ser Ser Ser Val Pro Val Ala Ser Ala
        1070                1075                1080 gtt gcg agt aga ctg tct tca cct gct gct tca tcg cga gta tcg     3294
Val Ala Ser Arg Leu Ser Ser Pro Ala Ala Ser Ser Arg Val Ser
1085                1090                1095 agc gct gtt tcg tct ctt gtc tcg tcg ggt ccc acg aaa cat gcc     3339
Ser Ala Val Ser Ser Leu Val Ser Ser Gly Pro Thr Lys His Ala
        1100                1105                1110 gcc ctt tca aat acg att tca tct gta gtg tcc caa gtt agt gca     3384
Ala Leu Ser Asn Thr Ile Ser Ser Val Val Ser Gln Val Ser Ala
1115                1120                1125 agt aac ccg ggg tta tcc gga tgc gac gtt ctc gtt cag gca ctc     3429
Ser Asn Pro Gly Leu Ser Gly Cys Asp Val Leu Val Gln Ala Leu
        1130                1135                1140 cta gaa gta gta tcc gcg ttg gtg agc atc tta taa                 3465
Leu Glu Val Val Ser Ala Leu Val Ser Ile Leu
1145                1150

<210> SEQ ID NO 2
<211> LENGTH: 1154
<212> TYPE: PRT
<213> ORGANISM: Artificial Sequence
<220> FEATURE:
<223> OTHER INFORMATION: Synthetic Construct

<400> SEQUENCE: 2

Met His His His His His His His His Ser Ser Gly Ser Ser
1               5                   10                  15

Leu Glu Val Leu Phe Gln Gly Pro Ala Arg Ala Gly Ser Gly Gln Gln
            20                  25                  30

Gly Pro Gly Gln Gln Gly Pro Gly Gln Gln Gly Pro Gly Gln Gln Gly
        35                  40                  45

Pro Tyr Gly Pro Gly Ala Ser Ala Ala Ala Ala Ala Gly Gly Tyr
    50                  55                  60

Gly Pro Gly Ser Gly Gln Gln Gly Pro Ser Gln Gln Gly Pro Gly Gln
65                  70                  75                  80

Gln Gly Pro Gly Gly Gln Gly Pro Tyr Gly Pro Gly Ala Ser Ala Ala
                85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ala Ala Ala Ala
        115                 120                 125

Ala Gly Gly Asn Gly Pro Gly Ser Gly Gln Gln Gly Ala Gln Gln
        130                 135                 140

Gly Pro Gly Gln Gln Gly Pro Gly Ala Ser Ala Ala Ala Ala Ala
145                 150                 155                 160

Gly Gly Tyr Gly Pro Gly Ser Gly Gln Gln Gly Pro Gly Gln Gln Gly
                165                 170                 175

Pro Gly Gly Gln Gly Pro Tyr Gly Pro Gly Ala Ser Ala Ala Ala Ala
            180                 185                 190
```

-continued

```
Ala Ala Gly Gly Tyr Gly Pro Gly Ser Gly Gln Gly Gln Gln
            195                 200             205
Gly Pro Gly Gly Gln Gly Pro Tyr Gly Pro Gly Ala Ser Ala Ala Ala
        210                 215                 220
Ala Ala Ala Gly Gly Tyr Gly Pro Gly Ser Gly Gln Gly Pro Gly
225                 230                 235                 240
Gln Gln Gly Pro Gly Gln Gln Gly Pro Gly Gln Gly Pro Tyr Gly
            245                 250                 255
Pro Gly Ala Ser Ala Ala Ala Ala Ala Gly Gly Tyr Gly Pro Gly
            260                 265                 270
Tyr Gly Gln Gln Gly Pro Gly Gln Gln Gly Pro Gly Gln Gly Pro
        275                 280                 285
Tyr Gly Pro Gly Ala Ser Ala Ala Ser Ala Ala Ser Gly Gly Tyr Gly
        290                 295                 300
Pro Gly Ser Gly Gln Gln Gly Pro Gly Gln Gln Gly Pro Gly Gln
305                 310                 315                 320
Gly Pro Tyr Gly Pro Gly Ala Ser Ala Ala Ala Ala Ala Gly Gly
            325                 330                 335
Tyr Gly Pro Gly Ser Gly Gln Gln Gly Pro Gly Gln Gln Gly Pro Gly
        340                 345                 350
Gln Gln Gly Pro Gly Gln Gln Gly Pro Gly Gln Gly Pro Tyr Gly
            355                 360                 365
Pro Gly Ala Ser Ala Ala Ala Ala Ala Gly Gly Tyr Gly Pro Gly
        370                 375                 380
Ser Gly Gln Gln Gly Pro Gly Gln Gln Gly Pro Gly Gln Gln Gly Pro
385                 390                 395                 400
Gly Gln Gln Gly Pro Gly Gln Gln Gly Pro Gly Gln Gln Gly Pro Gly
            405                 410                 415
Gln Gln Gly Pro Gly Gln Gln Gly Pro Gly Gln Gln Gly Pro Gly Gly
                420                 425                 430
Gln Gly Ala Tyr Gly Pro Gly Ala Ser Ala Ala Ala Gly Ala Ala Gly
            435                 440                 445
Gly Tyr Gly Pro Gly Ser Gly Gln Gln Gly Pro Gly Gln Gln Gly Pro
        450                 455                 460
Gly Gln Gln Gly Pro Gly Gln Gln Gly Pro Gly Gln Gln Gly Pro Gly
465                 470                 475                 480
Gln Gln Gly Pro Gly Gln Gln Gly Pro Gly Gln Gln Gly Pro Tyr Gly
            485                 490                 495
Pro Gly Ala Ser Ala Ala Ala Ala Ala Gly Gly Tyr Gly Pro Gly
            500                 505                 510
Ser Gly Gln Gln Gly Pro Gly Gln Gln Gly Pro Gly Gln Gln Gly Pro
        515                 520                 525
Gly Gly Gln Gly Pro Tyr Gly Pro Gly Ala Ala Ser Ala Ala Val Ser
        530                 535                 540
Val Ser Arg Ala Arg Ala Gly Ser Gly Gln Gln Gly Pro Gly Gln Gln
545                 550                 555                 560
Gly Pro Gly Gln Gln Gly Pro Gly Gln Gln Gly Pro Tyr Gly Pro Gly
            565                 570                 575
Ala Ser Ala Ala Ala Ala Ala Ala Gly Gly Tyr Gly Pro Gly Ser Gly
            580                 585                 590
Gln Gln Gly Pro Ser Gln Gln Gly Pro Gly Gln Gln Gly Pro Gly Gly
        595                 600                 605
Gln Gly Pro Tyr Gly Pro Gly Ala Ser Ala Ala Ala Ala Ala Ala Gly
```

```
                610             615             620
Gly Tyr Gly Pro Gly Ser Gly Gln Gln Gly Pro Gly Gln Gly Pro
625             630             635             640

Tyr Gly Pro Gly Ser Ser Ala Ala Ala Ala Ala Gly Gly Asn Gly
            645             650             655

Pro Gly Ser Gly Gln Gln Gly Ala Gln Gln Gly Pro Gly Gln Gln
            660             665             670

Gly Pro Gly Ala Ser Ala Ala Ala Ala Ala Gly Gly Tyr Gly Pro
            675             680             685

Gly Ser Gly Gln Gln Gly Pro Gly Gln Gln Gly Pro Gly Gln Gly
690             695             700

Pro Tyr Gly Pro Gly Ala Ser Ala Ala Ala Ala Ala Gly Gly Tyr
705             710             715             720

Gly Pro Gly Ser Gly Gln Gly Pro Gly Gln Gln Gly Pro Gly Gln
            725             730             735

Gly Pro Tyr Gly Pro Gly Ala Ser Ala Ala Ala Ala Ala Gly Gly
            740             745             750

Tyr Gly Pro Gly Ser Gly Gln Gln Gly Pro Gly Gln Gln Gly Pro
            755             760             765

Gly Gln Gln Gly Pro Gly Gly Gln Gly Pro Tyr Gly Pro Gly Ala Ser Ala
770             775             780

Ala Ala Ala Ala Ala Gly Gly Tyr Gly Pro Gly Tyr Gly Gln Gln Gly
785             790             795             800

Pro Gly Gln Gln Gly Pro Gly Gln Gly Pro Tyr Gly Pro Gly Ala
            805             810             815

Ser Ala Ala Ser Ala Ala Ser Gly Gly Tyr Gly Pro Gly Ser Gly Gln
            820             825             830

Gln Gly Pro Gly Gln Gln Gly Pro Gly Gln Gly Pro Tyr Gly Pro
            835             840             845

Gly Ala Ser Ala Ala Ala Ala Ala Gly Gly Tyr Gly Pro Gly Ser
850             855             860

Gly Gln Gln Gly Pro Gly Gln Gln Gly Pro Gly Gln Gln Gly Pro Gly
865             870             875             880

Gln Gln Gly Pro Gly Gly Gln Gly Pro Tyr Gly Pro Gly Ala Ser Ala
            885             890             895

Ala Ala Ala Ala Gly Gly Tyr Gly Pro Gly Ser Gly Gln Gln Gly
            900             905             910

Pro Gly Gln Gln Gly Pro Gly Gln Gln Gly Pro Gly Gln Gln Gly Pro
            915             920             925

Gly Gln Gln Gly Pro Gly Gln Gln Gly Pro Gly Gln Gln Gly Pro Gly
930             935             940

Gln Gln Gly Pro Gly Gln Gln Gly Pro Gly Gln Gly Ala Tyr Gly
945             950             955             960

Pro Gly Ala Ser Ala Ala Ala Gly Ala Ala Gly Gly Tyr Gly Pro Gly
            965             970             975

Ser Gly Gln Gln Gly Pro Gly Gln Gln Gly Pro Gly Gln Gln Gly Pro
            980             985             990

Gly Gln Gln Gly Pro Gly Gln Gln Gly Pro Gly Gln Gln Gly Pro Gly
            995             1000            1005

Gln Gln Gly Pro Gly Gln Gln Gly Pro Tyr Gly Pro Gly Ala Ser
            1010            1015            1020

Ala Ala Ala Ala Ala Ala Gly Gly Tyr Gly Pro Gly Ser Gly Gln
            1025            1030            1035
```

Gln Gly Pro Gly Gln Gln Gly Pro Gly Gln Gln Gly Pro Gly Gly
        1040                1045                1050

Gln Gly Pro Tyr Gly Pro Gly Ala Ala Ser Ala Ala Val Ser Val
        1055                1060                1065

Gly Gly Tyr Gly Pro Gln Ser Ser Ser Val Pro Val Ala Ser Ala
    1070                1075                1080

Val Ala Ser Arg Leu Ser Ser Pro Ala Ala Ser Ser Arg Val Ser
    1085                1090                1095

Ser Ala Val Ser Ser Leu Val Ser Ser Gly Pro Thr Lys His Ala
    1100                1105                1110

Ala Leu Ser Asn Thr Ile Ser Ser Val Val Ser Gln Val Ser Ala
    1115                1120                1125

Ser Asn Pro Gly Leu Ser Gly Cys Asp Val Leu Val Gln Ala Leu
    1130                1135                1140

Leu Glu Val Val Ser Ala Leu Val Ser Ile Leu
    1145                1150

<210> SEQ ID NO 3
<211> LENGTH: 636
<212> TYPE: PRT
<213> ORGANISM: Araneus diadematus

<400> SEQUENCE: 3

Ala Arg Ala Gly Ser Gly Gln Gln Gly Pro Gly Gln Gln Gly Pro Gly
1               5                   10                  15

Gln Gln Gly Pro Gly Gln Gln Gly Pro Tyr Gly Pro Gly Ala Ser Ala
            20                  25                  30

Ala Ala Ala Ala Ala Gly Gly Tyr Gly Pro Gly Ser Gly Gln Gln Gly
        35                  40                  45

Pro Ser Gln Gln Gly Pro Gly Gln Gln Gly Pro Gly Gln Gln Gly Pro
    50                  55                  60

Tyr Gly Pro Gly Ala Ser Ala Ala Ala Ala Ala Gly Gly Tyr Gly
65                  70                  75                  80

Pro Gly Ser Gly Gln Gln Gly Pro Gly Gly Gln Gly Pro Tyr Gly Pro
                85                  90                  95

Gly Ser Ser Ala Ala Ala Ala Ala Gly Gly Asn Gly Pro Gly Ser
            100                 105                 110

Gly Gln Gln Gly Ala Gly Gln Gln Gly Pro Gly Gln Gln Gly Pro Gly
        115                 120                 125

Ala Ser Ala Ala Ala Ala Ala Gly Gly Tyr Gly Pro Gly Ser Gly
    130                 135                 140

Gln Gln Gly Pro Gly Gln Gln Gly Pro Gly Gly Gln Gly Pro Tyr Gly
145                 150                 155                 160

Pro Gly Ala Ser Ala Ala Ala Ala Ala Gly Gly Tyr Gly Pro Gly
                165                 170                 175

Ser Gly Gln Gly Pro Gly Gln Gln Gly Pro Gly Gly Gln Gly Pro Tyr
            180                 185                 190

Gly Pro Gly Ala Ser Ala Ala Ala Ala Ala Gly Gly Tyr Gly Pro
        195                 200                 205

Gly Ser Gly Gln Gln Gly Pro Gly Gln Gln Gly Pro Gly Gln Gln Gly
    210                 215                 220

Pro Gly Gly Gln Gly Pro Tyr Gly Pro Gly Ala Ser Ala Ala Ala Ala
225                 230                 235                 240

Ala Ala Gly Gly Tyr Gly Pro Gly Tyr Gly Gln Gln Gly Pro Gly Gln

```
             245                 250                 255
Gln Gly Pro Gly Gly Gln Gly Pro Tyr Gly Pro Gly Ala Ser Ala Ala
            260                 265                 270

Ser Ala Ala Ser Gly Gly Tyr Gly Pro Gly Ser Gly Gln Gln Gly Pro
            275                 280                 285

Gly Gln Gln Gly Pro Gly Gln Gln Gly Pro Tyr Gly Pro Gly Ala Ser
            290                 295                 300

Ala Ala Ala Ala Ala Ala Gly Gly Tyr Gly Pro Gly Ser Gly Gln Gln
305                 310                 315                 320

Gly Pro Gly Gln Gln Gly Pro Gly Gln Gln Gly Pro Gly Gln Gln Gly
                325                 330                 335

Pro Gly Gly Gln Gly Pro Tyr Gly Pro Gly Ala Ser Ala Ala Ala Ala
            340                 345                 350

Ala Ala Gly Gly Tyr Gly Pro Gly Ser Gly Gln Gln Gly Pro Gly Gln
            355                 360                 365

Gln Gly Pro Gly Gln Gln Gly Pro Gly Gln Gln Gly Pro Gly Gln Gln
            370                 375                 380

Gly Pro Gly Gln Gln Gly Pro Gly Gln Gln Gly Pro Gly Gln Gln Gly
385                 390                 395                 400

Pro Gly Gln Gln Gly Pro Gly Gly Gln Gly Ala Tyr Gly Pro Gly Ala
                405                 410                 415

Ser Ala Ala Ala Gly Ala Ala Gly Gly Tyr Gly Pro Gly Ser Gly Gln
            420                 425                 430

Gln Gly Pro Gly Gln Gln Gly Pro Gly Gln Gln Gly Pro Gly Gln Gln
            435                 440                 445

Gly Pro Gly Gln Gln Gly Pro Gly Gln Gln Gly Pro Gly Gln Gln Gly
            450                 455                 460

Pro Gly Gln Gln Gly Pro Tyr Gly Pro Gly Ala Ser Ala Ala Ala Ala
465                 470                 475                 480

Ala Ala Gly Gly Tyr Gly Pro Gly Ser Gly Gln Gln Gly Pro Gly Gln
                485                 490                 495

Gln Gly Pro Gly Gln Gln Gly Pro Gly Gly Gln Gly Pro Tyr Gly Pro
            500                 505                 510

Gly Ala Ala Ser Ala Ala Val Ser Val Gly Gly Tyr Gly Pro Gln Ser
            515                 520                 525

Ser Ser Val Pro Val Ala Ser Ala Val Ala Ser Arg Leu Ser Ser Pro
            530                 535                 540

Ala Ala Ser Ser Arg Val Ser Ser Ala Val Ser Ser Leu Val Ser Ser
545                 550                 555                 560

Gly Pro Thr Lys His Ala Ala Leu Ser Asn Thr Ile Ser Ser Val Val
                565                 570                 575

Ser Gln Val Ser Ala Ser Asn Pro Gly Leu Ser Gly Cys Asp Val Leu
            580                 585                 590

Val Gln Ala Leu Leu Glu Val Val Ser Ala Leu Val Ser Ile Leu Gly
            595                 600                 605

Ser Ser Ser Ile Gly Gln Ile Asn Tyr Gly Ala Ser Ala Gln Tyr Thr
            610                 615                 620

Gln Met Val Gly Gln Ser Val Ala Gln Ala Leu Ala
625                 630                 635

<210> SEQ ID NO 4
<211> LENGTH: 2190
<212> TYPE: DNA
<213> ORGANISM: Araneus diadematus
```

<400> SEQUENCE: 4

```
agatatacat aatgcaccac catcaccacc atcatcacca tcatagcagc ggcagcagcc      60
tggaagttct gtttcagggt ccggcgcgtg cgggtagcgg ccagcagggc ccgggtcagc     120
agggtccggg ccaacaaggt ccgggccagc agggcccgta tggtccgggt gcaagcgcag     180
cagcagcggc cgcaggcggt tacggcccgg gtagcggcca gcagggcccg agccagcagg     240
gcccgggcca gcagggtccg ggcggtcagg gtccgtacgg tccgggcgcg agcgcggccg     300
ccgcggccgc aggcggttac gggccgggca gcggtcagca gggcccgggc ggtcagggcc     360
cgtatggccc gggtagcagc gcggccgcgg cggccgcagg cggtaatggt ccgggcagcg     420
gccagcaggg tgcgggccaa caaggcccgg gtcagcaggg cccgggtgcc agcgccgccg     480
cagcggccgc aggcggttac ggtccgggta gcggtcagca gggtcctggc caacaaggcc     540
cgggcggtca aggtccttac ggcccgggcg ccagcgccgc ggctgcggcc gcaggcggtt     600
acggaccggg tagcggccag ggtcctggtc aacaaggtcc gggcggtcaa ggcccgtatg     660
gtccgggcgc cagcgcggcg ccgcggccg caggcggtta cgggccaggt agcggccagc     720
agggtcctgg ccagcaggt cctgacaac aaggaccggg cggtcaagga ccgtacggcc     780
cgggcgcgag cgccgcggca gcggccgcag gcggttatgg tccgggttac ggtcagcagg     840
gtccggtca acaggaccg ggcggtcaag gtccgtatgg cccgggtgcg agcgcggcca     900
gcgcagcgag cggcggttac ggtcctggtt ctggtcagca gggtcctgga cagcaaggtc     960
cgggcggtca gggaccttac ggtccgggtg cgagcgccgc agcggccgca gcgggcggtt    1020
acggccctgg ctctggtcag cagggtccag gtcaacaggg tcctggtcaa cagggtcccg    1080
gtcagcaagg cccgggcggt cagggtcctt atggtccggg cgcaagcgcg ccgccgccg    1140
cagcgggcgg ttacggtcct ggcagtggtc agcagggtcc gggacaacag gtcctggac    1200
agcagggtcc tgggcagcag ggtcctggtc agcaaggtcc tggtcagcag ggccctggcc    1260
agcagggtcc cggtcagcag ggccctggtc aacaaggacc gggcggtcag ggcgcgtatg    1320
gtccgggtgc cagcgccgca gcgggcgccg caggcggtta cgggcctggt agtggtcaac    1380
aggggcctgg ccaacagggc cctggtcagc aaggccctgg tcaacagggc cctggtcagc    1440
agggccccgg tcaacagggc cccggtcaac agggtccagg tcagcaaggt ccgtacggcc    1500
cgggcgcaag cgccgcggca gcggccgcag gcggttacgg gcccggctct ggtcaacagg    1560
ggcccggtca acagggccca ggtcaacagg ggcgggcgg tcaagggcct tatggcccgg    1620
gcgccgcgag cgccgccgtg agcgttggcg gttacggtcc gcagagcagc agcgtgccgg    1680
ttgccagcgc agtggccagc cgcctgagca gcccggccgc gagcagccgt gtgagcagcg    1740
cagttagcag cttagtgagc agcggtccga ccaaacatgc cgcgctgagc aacacgatta    1800
gcagcgtggt tagccaggtt tctgcaagca atccgggtct gagcggttgc gatgtgctgg    1860
ttcaggcgct gctggaagtg gttagcgcct tagtgagcat cctgggcagc agcagcattg    1920
gccagatcaa ttatggcgcg agcgcccagt acacccagat ggttggtcag agcgtggcac    1980
aggccctggc gtgaaattcg agctccgtcg acaagcttgc ggccgcactc gagcaccacc    2040
accaccacca ctgagatccg gctgctaaca aagcccgaaa ggaagctgag ttggctgctg    2100
ccaccgctga gcaataacta gcataacccc ttggggcctc taaacgggtc ttgagggggtt    2160
ttttgctgaa aggaggaact atatccggat                                      2190
```

<210> SEQ ID NO 5

```
<211> LENGTH: 660
<212> TYPE: PRT
<213> ORGANISM: Araneus diadematus

<400> SEQUENCE: 5
```

| | | | | | | | | | | | | | | |
|---|---|---|---|---|---|---|---|---|---|---|---|---|---|---|
|Met|His|His|His|His|His|His|His|His|His|Ser|Ser|Gly|Ser|Ser|
|1| | | |5| | | | |10| | | | |15|

| | | | | | | | | | | | | | | |
|---|---|---|---|---|---|---|---|---|---|---|---|---|---|---|
|Leu|Glu|Val|Leu|Phe|Gln|Gly|Pro|Ala|Arg|Ala|Gly|Ser|Gly|Gln|Gln|
| | | |20| | | |25| | | |30| | | |

Gly Pro Gly Gln Gln Gly Pro Gly Gln Gln Gly Pro Gly Gln Gln Gly
            35                  40                  45

Pro Tyr Gly Pro Gly Ala Ser Ala Ala Ala Ala Ala Gly Gly Tyr
    50                  55                  60

Gly Pro Gly Ser Gly Gln Gln Gly Pro Ser Gln Gly Pro Gly Gln
65                  70                  75                  80

Gln Gly Pro Gly Gly Gln Gly Pro Tyr Gly Pro Gly Ala Ser Ala Ala
            85                  90                  95

Ala Ala Ala Ala Gly Gly Tyr Gly Pro Gly Ser Gly Gln Gln Gly Pro
            100                 105                 110

Gly Gly Gln Gly Pro Tyr Gly Pro Gly Ser Ser Ala Ala Ala Ala
            115                 120                 125

Ala Gly Gly Asn Gly Pro Gly Ser Gly Gln Gln Gly Ala Gly Gln Gln
            130                 135                 140

Gly Pro Gly Gln Gln Gly Pro Gly Ala Ser Ala Ala Ala Ala Ala Ala
145                 150                 155                 160

Gly Gly Tyr Gly Pro Gly Ser Gly Gln Gln Gly Pro Gly Gln Gln Gly
            165                 170                 175

Pro Gly Gly Gln Gly Pro Tyr Gly Pro Gly Ala Ser Ala Ala Ala Ala
            180                 185                 190

Ala Ala Gly Gly Tyr Gly Pro Gly Ser Gly Gln Gly Pro Gly Gln Gln
            195                 200                 205

Gly Pro Gly Gly Gln Gly Pro Tyr Gly Pro Gly Ala Ser Ala Ala Ala
            210                 215                 220

Ala Ala Ala Gly Gly Tyr Gly Pro Gly Ser Gly Gln Gln Gly Pro Gly
225                 230                 235                 240

Gln Gln Gly Pro Gly Gln Gln Gly Pro Gly Gly Gln Gly Pro Tyr Gly
            245                 250                 255

Pro Gly Ala Ser Ala Ala Ala Ala Ala Gly Gly Tyr Gly Pro Gly
            260                 265                 270

Tyr Gly Gln Gln Gly Pro Gly Gln Gln Gly Pro Gly Gly Gln Gly Pro
            275                 280                 285

Tyr Gly Pro Gly Ala Ser Ala Ala Ser Ala Ala Ser Gly Gly Tyr Gly
            290                 295                 300

Pro Gly Ser Gly Gln Gln Gly Pro Gly Gln Gln Gly Pro Gly Gly Gln
305                 310                 315                 320

Gly Pro Tyr Gly Pro Gly Ala Ser Ala Ala Ala Ala Ala Gly Gly
            325                 330                 335

Tyr Gly Pro Gly Ser Gly Gln Gln Gly Pro Gly Gln Gln Gly Pro Gly
            340                 345                 350

Gln Gln Gly Pro Gly Gln Gln Gly Pro Gly Gly Gln Gly Pro Tyr Gly
            355                 360                 365

Pro Gly Ala Ser Ala Ala Ala Ala Ala Ala Gly Gly Tyr Gly Pro Gly
            370                 375                 380

Ser Gly Gln Gln Gly Pro Gly Gln Gln Gly Pro Gly Gln Gln Gly Pro

```
385                 390                 395                 400
Gly Gln Gln Gly Pro Gly Gln Gln Gly Pro Gly Gln Gln Gly Pro Gly
                405                 410                 415
Gln Gln Gly Pro Gly Gln Gln Gly Pro Gly Gln Gln Gly Pro Gly Gly
            420                 425                 430
Gln Gly Ala Tyr Gly Pro Gly Ala Ser Ala Ala Ala Gly Ala Ala Gly
        435                 440                 445
Gly Tyr Gly Pro Gly Ser Gly Gln Gln Gly Pro Gly Gln Gln Gly Pro
    450                 455                 460
Gly Gln Gln Gly Pro Gly Gln Gln Gly Pro Gly Gln Gln Gly Pro Gly
465                 470                 475                 480
Gln Gln Gly Pro Gly Gln Gln Gly Pro Gly Gln Gln Gly Pro Tyr Gly
                485                 490                 495
Pro Gly Ala Ser Ala Ala Ala Ala Ala Gly Gly Tyr Gly Pro Gly
            500                 505                 510
Ser Gly Gln Gln Gly Pro Gly Gln Gln Gly Pro Gly Gln Gln Gly Pro
        515                 520                 525
Gly Gly Gln Gly Pro Tyr Gly Pro Gly Ala Ala Ser Ala Ala Val Ser
    530                 535                 540
Val Gly Gly Tyr Gly Pro Gln Ser Ser Ser Val Pro Val Ala Ser Ala
545                 550                 555                 560
Val Ala Ser Arg Leu Ser Ser Pro Ala Ala Ser Ser Arg Val Ser Ser
                565                 570                 575
Ala Val Ser Ser Leu Val Ser Ser Gly Pro Thr Lys His Ala Ala Leu
            580                 585                 590
Ser Asn Thr Ile Ser Ser Val Val Ser Gln Val Ser Ala Ser Asn Pro
        595                 600                 605
Gly Leu Ser Gly Cys Asp Val Leu Val Gln Ala Leu Leu Glu Val Val
    610                 615                 620
Ser Ala Leu Val Ser Ile Leu Gly Ser Ser Ser Ile Gly Gln Ile Asn
625                 630                 635                 640
Tyr Gly Ala Ser Ala Gln Tyr Thr Gln Met Val Gly Gln Ser Val Ala
                645                 650                 655
Gln Ala Leu Ala
        660
```